(12) United States Patent
Shuster et al.

(10) Patent No.: US 8,980,548 B2
(45) Date of Patent: Mar. 17, 2015

(54) METHODS AND REAGENTS FOR METABOLOMICS AND HISTOLOGY IN A BIOLOGICAL SAMPLE AND A KIT FOR THE SAME

(75) Inventors: Jeffrey Richard Shuster, Chapel Hill, NC (US); Klaus Peter Adam, Cary, NC (US); Danny Carroll Alexander, Cary, NC (US); Dean A. Troyer, Norfolk, VA (US); Raymond S. Lance, Virginia Beach, VA (US)

(73) Assignees: Metabolon, Inc., Durham, NC (US); Eastern Virginia Medical School, Norfolk, VA (US)

( * ) Notice: Subject to any disclaimer, the term of this patent is extended or adjusted under 35 U.S.C. 154(b) by 73 days.

(21) Appl. No.: 13/698,116

(22) PCT Filed: May 19, 2011

(86) PCT No.: PCT/US2011/037093
§ 371 (c)(1),
(2), (4) Date: Jan. 25, 2013

(87) PCT Pub. No.: WO2011/146683
PCT Pub. Date: Nov. 24, 2011

(65) Prior Publication Data
US 2013/0115649 A1      May 9, 2013

Related U.S. Application Data

(60) Provisional application No. 61/346,228, filed on May 19, 2010.

(51) Int. Cl.
*C12Q 1/68* (2006.01)
*G01N 33/50* (2006.01)

(52) U.S. Cl.
CPC .................. *G01N 33/5091* (2013.01)

USPC .............................................. 435/6; 435/7.23

(58) Field of Classification Search
CPC .................. C12Q 1/68; A61Q 19/08
USPC ...................................... 435/6, 7.23
See application file for complete search history.

(56) References Cited

U.S. PATENT DOCUMENTS

| | | |
|---|---|---|
| 6,025,128 A | 2/2000 | Veltri et al. |
| 2003/0119049 A1 | 6/2003 | Lorincz et al. |
| 2004/0081979 A1 | 4/2004 | Knezevic et al. |
| 2005/0255491 A1 | 11/2005 | Lee et al. |
| 2008/0268451 A1 | 10/2008 | Seligmann et al. |
| 2009/0047269 A1 | 2/2009 | Chinnaiyan et al. |

OTHER PUBLICATIONS

Chan et al. "Metabolic profiling of human colorectal cancer using high-resolution magic angle spining nuclear magnetic resonance (HR-MAS-NMR) spectroscopy and gas chromatography mass spectrometry (GC-MS)", J of Proteome Research, 2009,8:352-361.*
Hood et al. "Proteomic analysis of formalin-fixed prostate cancer tissue", Molecular & Cellular Proteomics, 2005, 4:1741-1753.*
Zhang et al. "An improvement method of extracting total RNA from spinal disc tissue", Sichuan Medical Journal, 2009, abstract only, 1 page.*
International Search Report for PCT/US11/37093, filed May 19, 2011.

* cited by examiner

*Primary Examiner* — Bin Shen
(74) *Attorney, Agent, or Firm* — Brinks Gilson & Lione

(57) ABSTRACT

A method of extracting and measuring one or more biochemicals from a biological sample, comprises immersing the biological sample in an organic solvent, whereby one or more biochemicals present in the biological sample are extracted into the organic solvent; separating the biological sample from the free organic solvent; and measuring the level(s) of the one or more biochemicals extracted into the organic solvent, wherein the biological sample remains analyzable by histological analysis.

24 Claims, 10 Drawing Sheets

METHODS AND REAGENTS FOR METABOLOMICS AND HISTOLOGY IN A BIOLOGICAL SAMPLE AND A KIT FOR THE SAME

This application is a National Stage application of International Application No. PCT/US2011/037093, filed May 19, 2011, which claims the benefit of U.S. Provisional Application No. 61/346,228, filed May 19, 2010.

BACKGROUND

Field

Metabolomics is a method by which the low molecular weight (<2 kD) biochemical compounds, (e.g., metabolites), present in a biological sample are extracted, detected and measured. The method has been successfully employed in the study of the biochemical basis and mechanisms for diverse biological processes such as cancer diagnosis and monitoring progression, drug mechanism of action, drug toxicity, industrial bio-processing, etc. Currently the extraction of metabolites for metabolomic analysis from a tissue or cellular sample involves extraction of the biochemicals by a physical disruption of the biological materials. This method precludes the ability to histologically analyze the same biological material for its architectural (morphological) characteristics, including, but not limited to, direct examination of cells and/or tissues by microscopic methods, histopathology analysis after tissue fixation and staining (for example by hematoxylin and eosin), immunohistochemistry analysis, fluorescence in situ hybridization, or using any other techniques known in the art.

Currently, biochemical extraction is destructive to the specimen being examined thus precluding histological evaluation of the same specimen. To perform a biochemical analysis and a tissue analysis of the same tissue or cell type, one portion of the biological material is examined by histological or cytological analysis, and a different portion of the biological specimen is used for the biochemical analysis. In many cases there is heterogeneity in a biological material being analyzed, thus it is beneficial to perform both a metabolomics analysis and a histological or cytological analysis on the exact same tissue or cell based specimen. For example, human tissues are comprised of different cell types and architectures. This is particularly true of clinical biopsy specimens for a disease state such as cancer. The purpose of a biopsy in clinical practice is to accurately diagnose by histology and to gauge aggressiveness of a diseased tissue such as those containing cancer. For example, often a biopsy pathology report will indicate such variable traits in the analysis as percent of the biopsy that is cancer, degree of invasion into different adjacent tissue types, and a qualitative assessment of the degree of cellular structural organization/disorganization. Various types of biopsies may be obtained. Suspected tissues may be surgically excised using either open or laparoscopic biopsies. Increasingly, core biopsies are used in lieu of a surgical procedure as they are more convenient, present less risk, and can be directed to suspected lesions using imaging.

It has been well described in the literature that different biopsy specimens coming from the same organ can show very different results upon histological analysis. In addition, results may vary with different pathologists. For example, Gleason scoring is a classification system in pathology used to assign a grade for prostatic adenocarcinomas (Epstein J I, Allsbrook W C, Amin M B, Egevad L L, ISUP Grading Committee. *The 2005 International Society of Urological Pathology (ISUP) Consensus Conference on Gleason Grading of Prostatic Carcinoma*. Am J Surg Pathol 29 (2005), 1228-1242). As such, it is subject to inter-observer variability in scoring depending on the experience of the pathologist rendering the diagnosis and performing the scoring (Oyama T, Allsbrook W C Jr, Kurokawa K, Matsuda H, Segawa A, Sano T, Suzuki K, Epstein J I. *A comparison of inter-observer reproducibility of Gleason grading of prostatic carcinoma in Japan and the United States*. Arch Pathol Lab Med. 2005 August; 129(8):1004-100).

Therefore, augmenting histopathologic evaluation of a tissue with a quantitative measure such as can be obtained by the determination of the levels of biochemicals (e.g., proteins, nucleic acids, metabolites, etc.) in a sample is needed. In the case of prostate cancer, certain biochemicals have been shown to correlate with cancer progression and the measurement of these and other compounds can be of use in the quantitation of disease aggressiveness (e.g., PCT Patent Application Publication No. WO2008036691A2; U.S. patent application Ser. No. 12/441,945; PCT Patent Application Publication No. WO2009026152A1; and US Patent Application Publication No. 2009/0075284).

Thus the development of a method(s) that can be used for the analysis of both the biochemical profile and the histology on the same biological specimen are needed.

SUMMARY

The present invention relates to methods for the extraction of biochemicals from a biological sample and subsequent analysis of the same biological sample by a method of histological analysis. In particular, the present invention provides methods for contacting a tissue specimen with an organic solvent that preserves the tissue in a manner compatible with histologic procedures and pathologic analysis, and assaying the solvent extract for biochemicals. In another aspect, the present invention provides methods for contacting cells with an organic solvent that preserves the cells in a manner compatible with cytologic procedures and/or pathologic analysis, and assaying the solvent extract for biochemicals.

In an aspect of the invention, a method of extracting and measuring one or more biochemicals from a biological sample, comprises immersing the biological sample in an organic solvent, whereby one or more biochemicals present in the biological sample are extracted into the organic solvent; separating the biological sample from the free organic solvent; and measuring a level(s) of the one or more biochemicals extracted into the organic solvent, wherein the biological sample remains analyzable by histological analysis.

In a feature of this aspect, the one or more biochemicals are one or more metabolites. In an embodiment, the one or more metabolites may be selected from Table 2, Table 12 and Table 15. The one or more biochemicals may be one or more proteins or peptides.

In a feature of this aspect, the biological sample is immersed for a predetermined period of time. In another feature, the one or more biochemicals is a xenobiotic.

In still another feature, the organic solvent comprises an alcohol. The organic solvent may comprise an aqueous solution of methanol. With regard to this feature, the aqueous solution of methanol may comprise from 60% to 80% methanol. The aqueous solution may comprise methanol and ethanol. The organic solvent may comprise an aqueous solution of ethanol. With regard to this feature, the aqueous solution of ethanol may comprise from 60% to 80% ethanol.

In other features, the biological sample may be tumor tissue, prostate tissue, or spinal disc tissue. In another feature, the method may further comprise performing histological analysis on the biological sample after it has been separated from the organic solvent. The histological analysis may comprise hematoxylin and eosin staining, immunohistochemistry, or cytological analysis.

In another aspect of the invention, a method for performing histological and metabolite analyses on the same biological sample comprises immersing the biological sample in an organic solvent for a pre-determined period of time, whereby one or more metabolites present in the biological sample are extracted into the organic solvent; removing the biological sample from the organic solvent; measuring a level(s) of the one or more metabolites extracted into the organic solvent; and performing histological analysis on the biological sample after it has been removed from the organic solvent.

In yet another aspect, the invention relates to a method for extraction and measurement of one or more metabolites from a biological sample without damaging the biological sample. In a further aspect, the invention relates to a method for extracting and measuring metabolites from tissue samples while retaining tissue morphology and utility for subsequent histological analyses. The invention may also relate to a method for disease diagnosis, prognosis, and monitoring. The invention also may relate to a kit providing reagents and components for performing the extracting and measuring method.

DETAILED DESCRIPTION

Figure 1:
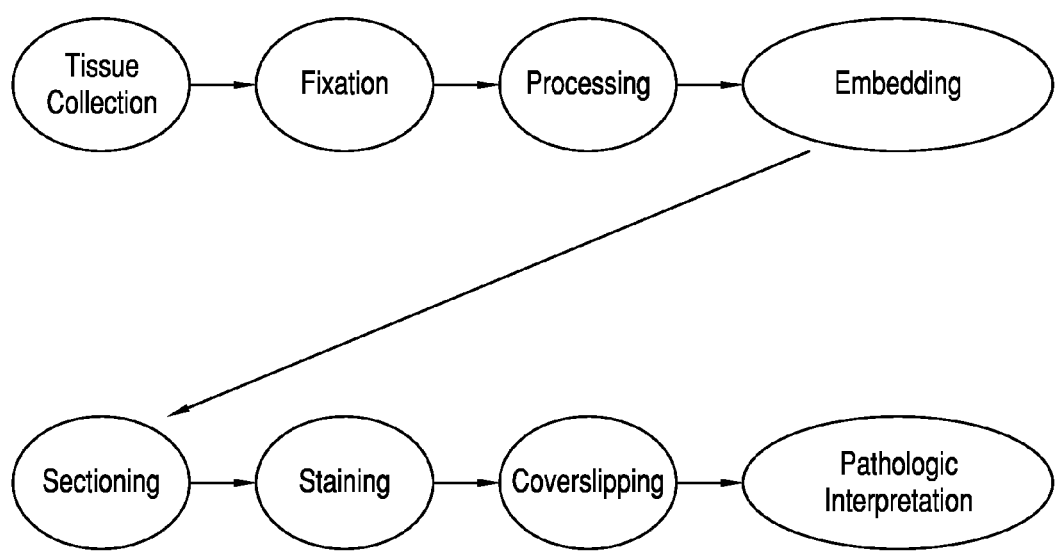
FIG. 1 provides a schema of histological analysis of tissue specimens.

The present invention relates to methods for the extraction of biochemicals from a biological sample and subsequent analysis of the same biological sample by a method of histological analysis. As used herein, the term "histological analysis" is used broadly to encompass the study of tissue samples such as using thin sections of a sample derived from a biological sample and also to include the study of cell samples (cytological analysis), such as cells samples in body fluids or cells from samples aspirated from the body or cells cultured in vitro. Exemplary biochemicals may include proteins and peptides, nucleic acids (including RNA, DNA, and microRNA), metabolites, and xenobiotics. Current practice involves destruction of the tissue sample from which the metabolite or biochemical is obtained. Often the sample is destroyed by grinding before the biochemicals are obtained therefrom. As a result, the tissue is not useful for histological assessment. Therefore, the objective of the instant invention is to provide a non-destructive method and a kit for performing biochemical, metabolomic and histological analyses on the same tissue sample.

Biological tissue material is fully or partially immersed in a solvent whereby the solvent can be recovered for the analysis of the extracted biochemicals contained therein, and the tissue, with its cellular architecture preserved, is subsequently analyzed using histological analysis methods (including cytological analysis). The biological sample is separated from the free organic solvent, which may include all or a portion of the total solvent (for example, some portion of the solvent may remain associated with the biological sample and therefore be separated therewith). In embodiments, solvents may include aqueous solutions of alcohols. For example, the solvents may be aqueous solutions of methanol and/or ethanol. Other or additional solvents may include aqueous solutions of glyoxal, acetone, isopropanol, and dichloromethane. In embodiments, the aqueous solutions may contain from about 40% to about 90% alcohol, from about 50% to about 85% alcohol, from about 60% to about 80% alcohol, and from about 70% to about 80% alcohol.

In embodiments, the histological methods may include hematoxylin and eosin staining (H&E), phosphotungstic acid hematoxylin staining, uranyl acetate and lead citrate staining, and immunohistochemistry (IHC) staining of proteins. In other embodiments, the histological methods may include fine-needle aspiration of samples from tumors. In one embodiment, the solvent is an aqueous solution of 70% methanol, and the histology is performed by hematoxylin and eosin staining and analysis. In another embodiment, the solvent is an aqueous solution of 70% ethanol, and the histology is performed by hematoxylin and eosin staining and analysis. In yet another embodiment, the solvent is an aqueous solution of ethanol or methanol, and the histology is performed by IHC staining and analysis.

The inventive method may be useful for diagnosing or aiding in the diagnosis of cancer, or determining the prognosis or aiding in determining the prognosis for cancer related illness, including but not limited to, characterizing risk of cancer, stage of cancer, risk of or presence of metastasis, invasiveness of cancer, aggressiveness of cancer, recurrence of cancer, etc. based on the presence of metabolites and histological or cytological analysis.

The inventive method may also be useful for assessing or aiding the assessment of the effect of treatments of tissues or cells with an agent, either to manage a disease state, or to retain a healthy state, including, but not limited to drug treatments, radiation treatments, heat or cryo-ablation, immunostimulation therapy, dietary modification, etc. Further, the inventive method may also be useful for assessing or aiding the assessment of the effect of therapeutic treatments of tissues or cells with an agent, for use as a method of screening compounds for therapeutic activity.

Additionally, the inventive method may also be useful for monitoring or aiding the monitoring of toxicity to a tissue or cells incurred by a natural or synthetic substance, or treatment, including, but not limited to liver toxicity, kidney toxicity, neuro-toxicity, etc. Further, the inventive method may also be useful for determining or aiding in the determination of the effects of treatments that result in a change in cell differentiation including, but not limited to a change of stem cells to a more differentiated state or a change of differentiated cells to a more stem cell-like state, etc.

In addition, the inventive method may also be useful for the diagnosing or aiding the diagnosis of transplanted tissue rejection, or determining or aiding in determining the prognosis thereof. The inventive method may also be useful for the diagnosing, aiding the diagnosis of and/or determining or aiding the determination of the prognosis of inflammatory skin diseases, including but not limited to characterizing the disease based on histology and metabolomic profile.

Further, the inventive method may also be useful for assessing or aiding in the assessment of obesity including but not limited to characterizing the disease based on histology and metabolomic profiles of core biopsies of fat and muscle. The inventive method may also be useful for assessing or aiding in assessing muscle and nerve diseases based upon histology and metabolomic profiles of muscle and nerve biopsies. The inventive method may also be useful for assessing or aiding in assessing lymphoid and hematopoietic malignancies based upon histology and metabolomic profiling.

The inventive method may also be useful for assessing or aiding in assessing the status of an allograft heart, liver, kidney, pancreas or other transplanted organ based upon histology and metabolomic profiling. Additionally, the inventive method may also be useful for assessing or aiding in assessing cytologic specimens such as needle aspirations based upon histology and metabolomic profiling. Examples include aspirations of lymph nodes, thyroid glands, breast, and masses. The inventive method may also be useful for assessing or aiding in assessing gastrointestinal biopsies for inflammatory bowel disease, malignancies, presence of microorganisms such as *H. pylori*, and dysplasia such as in Barrett's esophagus.

DEFINITIONS

The term "Solvent Extraction of Metabolites", abbreviated "SEM", refers to the immersion of a biological tissue or cellular material in a solution containing an organic solvent whereby metabolites are extracted into the solvent for analysis while tissue and/or cell structures are retained suitable for histological analysis.

The term Preservation by Extraction and Fixation, abbreviated "PREF", refers to a process of preserving cellular structure in tissue or cell specimens whilst extracting small molecules by immersing the tissue in a solution containing an organic solvent, then subsequently processing the exact same portion of tissue using histological methods. PREF enables both quantitation of biochemicals, including small molecule metabolites, and histological examination of the same tissue sample.

The term "Histology" refers to the scientific study of the microscopic anatomy of cells and tissues of plants and animals. Histological study may be performed by the preparation of a thin section(s) of a sample derived from a biological sample of an animal, plant, or synthetic material that can be examined under a microscope. Histological study includes preparation of sections to be examined by immunofluorescence or immunohistochemistry (IHC) for in situ detection of proteins; by in-situ methods such as fluorescent in situ (FISH) or chromogenic in situ hybridization (CISH) which use both direct and indirect methods for labeling nucleic acid probes after hybridization with target DNA or RNA for detection of DNA, RNA, and alterations therein. Histological study includes preparation of paraffin embedded sample sections and cryosections wherein 4-5 micron thick sections of a flash frozen sample are prepared using a cryostat. The cryosections are then fixed in alcohol, re-hydrated, and directly stained with a histological stain. An exemplary stain is hematoxylin and eosin. Cryosections of frozen tissue offer better preservation of proteins and nucleic acids with some sacrifice in morphology. Cryosections are used in methods for in situ detection of proteins such as targeted or matrix assisted imaging mass spectroscopy or in situ detection of nucleic acids such as combined with laser capture microscopy. In addition, cryosections can be directly extracted for analysis of nucleic acids and proteins.

"Cytology" refers to the study of cells. In the medical specialty of pathology, cytology refers to making diagnoses of disease and conditions by performing cytological examinations on body fluids (e.g., blood, urine, cerebrospinal fluid) or on samples aspirated (drawn out via suction into a syringe) from the body. Non-limiting examples include evaluation of cervical smears used in the Pap test for cervical cancer and fine-needle aspirants from tumors to determine the presence or absence of, for example, lung or prostate cancer. To carry out cytological examinations, the material can be spread onto glass slides, fixed and stained. The prepared slides are then examined microscopically by a pathologist.

"Biochemical" includes any molecule that is related to biology that can be extracted using the methods described. Exemplary biochemicals include, but are not limited to, proteins and peptides, nucleic acids (including RNA, DNA, and microRNAs), metabolites, and xenobiotics.

"Sample" or "biological sample" or "specimen" means any biological material isolated from a subject suitable for detecting the desired biomarkers and for performing histology analyses and may comprise cellular material from the subject. The sample can be isolated from any suitable biological tissue or biopsy such as, for example, adipose tissue, cardiac tissue, liver tissue, lung tissue, tissue of the gastrointestinal tract (e.g., esophagus, intestine, intestinal polyps, colon, etc.), kidney tissue, bladder tissue, tumor tissue (cancerous or non-cancerous, benign), thyroid tissue, muscle tissue, prostate tissue, skin, blood, etc.

"Subject" means any animal, but is preferably a mammal, such as, for example, a human, monkey, non-human primate, rat, mouse, cow, dog, cat, pig, horse, or rabbit.

"Biomarker" means a compound, preferably a metabolite, that is differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (e.g., a p-value less than 0.05 and/or a q-value of less than 0.10 as determined using either Welch's T-test or Wilcoxon's rank-sum Test). Alternatively, a biomarker can demonstrate a correlation with a given disorder or clinical measurement. The range of possible correlations is between negative (−) 1 and positive (+) 1. A result of negative (−) 1 means a perfect negative correlation and a positive (+) 1 means a perfect positive correlation, and 0 means no correlation at all. A "substantial positive correlation" refers to a biomarker having a correlation from +0.25 to +1.0 with a disorder or with a clinical measurement, while a "substantial negative correlation" refers to a correlation from −0.25 to −1.0 with a given disorder or clinical measurement. A "significant positive correlation" refers to a biomarker having a correlation of from +0.5 to +1.0 with a given disorder or clinical measurement, while a "significant negative correlation" refers to a correlation to a disorder of from −0.5 to −1.0 with a given disorder or clinical measurement.

"Non-biomarker compound" means a compound that is not differentially present in a biological sample from a subject or a group of subjects having a first phenotype (e.g., having a first disease) as compared to a biological sample from a subject or group of subjects having a second phenotype (e.g., not having the first disease). Such non-biomarker compounds may, however, be biomarkers in a biological sample from a subject or a group of subjects having a third phenotype (e.g., having a second disease) as compared to the first phenotype (e.g., having the first disease) or the second phenotype (e.g., not having the first disease).

The "level" of one or more biomarkers means the absolute or relative amount or concentration of the biomarker in the sample.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, a "cancer-positive reference level" of a biomarker means a level of a biomarker that is indicative of a positive diagnosis of cancer in a subject, and a "cancer-negative reference level" of a biomarker means a level of a biomarker that is indicative of a negative diagnosis of cancer in a subject. As another example, a "cancer-progression-positive reference level" of a biomarker means a level of a biomarker that is indicative of progression of cancer in a subject, and a "cancer-regression-positive reference level" of a biomarker means a level of a biomarker that is indicative of regression of cancer. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. A "reference level" may also be a "standard curve reference level" based on the levels of one or more biomarkers determined from a population and plotted on appropriate axes to produce a reference curve (e.g. a standard probability curve). Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). A standard curve reference level may be determined from a group of reference levels from a group of subjects having a particular disease state, phenotype, or lack thereof (e.g. known cancer) using statistical analysis, such as univariate or multivariate regression analysis, logistic regression analysis, linear regression analysis, and the like of the levels of such biomarkers in samples from the group. Such reference levels may also be tailored to specific techniques that are used to measure levels of biomarkers in biological samples (e.g., LC-MS, GC-MS, NMR, enzyme assays, etc.), where the levels of biomarkers may differ based on the specific technique that is used.

"Metabolite", or "small molecule", means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell.

"Metabolic profile", or "small molecule profile", means a complete or partial inventory of small molecules within a targeted cell, tissue, organ, organism, or fraction thereof (e.g., cellular compartment). The inventory may include the quantity and/or type of small molecules present. The "small molecule profile" may be determined using a single technique or multiple different techniques. The techniques may include targeted assays that are directed to one or more specific small molecule(s) such as a panel of biomarkers useful for determining the presence or absence of a disease state or a panel of biomarkers that are indicative of the status of cellular metabolism.

"Metabolome" means all of the small molecules present in a given organism.

I. Applications

The disclosed methods are useful for, but not limited to, the following applications.

In one embodiment, the present invention provides a method of analyzing prostate biopsy specimens for the presence and degree of aggressiveness of prostate cancer. The method comprises contacting prostate biopsy specimens with a solvent solution. The solvent solution may comprise 70% methanol or 70% ethanol. The metabolites extracted into the solvent solution are analyzed by mass spectrometry. The tissue that was contacted with the solvent solution is subsequently stained with hematoxylin and eosin and the tissue architecture examined under a microscope in order to determine the presence and degree of aggressiveness of prostate cancer from both metabolite and histological analysis from the same biopsy specimen.

In some embodiments, the present invention provides methods for the diagnosing or aiding in the diagnosis of cancer, or determining the prognosis or aiding in determining the prognosis for cancer related illness, including but not limited to, characterizing risk of cancer, stage of cancer, risk of or presence of metastasis, invasiveness of cancer, aggressiveness of cancer, recurrence of cancer, etc. based on the presence of metabolites in a specimen and histological analysis of the same specimen.

In another embodiment, the present invention provides methods for assessing or aiding the assessment of the effect of treatments of tissues or cells with an agent, either to manage a disease state, to retain a healthy state, including, but not limited to drug treatments, radiation treatments, heat or cryo-ablation, immuno-stimulation therapy, dietary modification, etc.

In another embodiment, the present invention provides methods for assessing or aiding the assessment of the effect of therapeutic treatments of tissues or cells with an agent, for use as a method of screening compounds for therapeutic activity.

In another embodiment, the present invention provides methods for monitoring or aiding the monitoring of toxicity to a tissue or cells incurred by a natural or synthetic substance, or treatment, including, but not limited to liver toxicity, kidney toxicity, neuro-toxicity, etc.

In another embodiment, the present invention provides methods for determining or aiding in the determination of the effects of treatments that result in a change in cell differentiation including, but not limited to a change of stem cells to a more differentiated state or a change of differentiated cells to a more stem cell-like state, etc.

In another embodiment, the present invention provides methods for the diagnosing or aiding the diagnosis of transplanted tissue rejection, or determining or aiding in determining the prognosis thereof.

In another embodiment, the present invention provides methods for the diagnosing, aiding the diagnosis of, and/or determining or aiding the determination of the prognosis of inflammatory skin diseases, including but not limited to characterizing the disease based on histology and metabolomic profile.

In another embodiment, the present invention provides methods for assessing or aiding in the assessment of obesity including but not limited to characterizing the disease based on histology and metabolomic profiles of core biopsies of fat and muscle.

In another embodiment, the present invention provides methods for assessing or aiding in assessing muscle and nerve diseases based upon histology and metabolomic profiles of muscle and nerve biopsies.

In another embodiment, the present invention provides methods for assessing or aiding in assessing lymphoid and hematopoietic malignancies based upon histology and metabolomic profiling.

In another embodiment, the present invention provides for assessing or aiding in assessing the status of an allograft heart, liver, kidney, pancreas or other transplanted organ based upon histology and metabolomic profiling.

In another embodiment, the present invention provides for assessing or aiding in assessing cytologic specimens such as needle aspirations based upon histology and metabolomic profiling. Examples include aspirations of lymph nodes, thyroid glands, breast, and masses.

In another embodiment, the present invention provides for assessing or aiding in assessing gastrointestinal biopsies for inflammatory bowel disease, malignancies, presence of microorganisms such as *H. pylori*, and dysplasia such as in Barrett's esophagus.

In another embodiment, the method may be used for analyzing spinal discs or other tissue types that are recalcitrant to grinding and metabolite extraction. Spinal discs are not amenable to grinding. Additionally, extraction of biochemicals therefrom is difficult, and results are variable. Further, when the extracts are injected onto Gas Chromatography (GC) or Liquid Chromatography (LC) columns, the columns clog and must be changed, which is costly in terms of the column expense, and the time required to replace the column and to recalibrate the instrument.

In another embodiment, the method may be used for analyzing cell cultures.

II. Sample Types

Any biological or synthetic sample that can be histologically sectioned or cytologically analyzed can be tested according to the methods described herein. By way of non-limiting examples, the sample may be a clinical biopsy specimen (e.g., a transrectal obtained prostate biopsy), a post-surgical specimen, in vitro cell culture material, blood or other body fluid-derived cellular material, transplanted tissues (including xenograph tissue), fine-needle aspirants, etc. In addition to animal derived materials, the method of the invention may be used for tissues and cells not of animal origin including those of plant, bacterial, and archaebacterial origins.

III. Extraction of Biochemicals while Preserving Tissue Morphology

Biochemicals may be extracted from tissues in, for example, a solvent by placing the tissue into a tube with the solvent to obtain a ratio of 0.25 ml of solvent per mg of weight wet tissue, and incubating the tissue in the solvent for various times (e.g., 1 hour, 2 hours, 3 hours, 6 hours, 12 hours, 24 hours, etc.) at room temperature, (e.g., between 22 and 24° C.). The solvent may include an aqueous solution of alcohol. For example, the solvent may be an aqueous solution of methanol and/or ethanol. Exemplary biochemicals that may be extracted are metabolites. Although the below description pertains to metabolites as an example, the method described herein should not be limited to metabolites. After the incubation step, the tissue sample is removed from the solvent and processed for histological analysis as exemplified below. The metabolites in the solvent are subjected to metabolomics analysis or measured using biochemical techniques. It is recognized that methanol and ethanol solvents may be used in different concentrations either alone or in combination with each other as long as the architecture of the tissue or cells remains suitable for histological analysis. It is also recognized that other organic solvents may be used as long as the solvent effectively extracts metabolites from the specimen without damaging the tissue or cells of the specimen such that the architecture of the tissue or cells remains suitable for, and can subsequently be analyzed by histological analysis. The preferred solvent type is a solvent that is capable of being concentrated by any means, such as evaporation (including to dryness) while leaving essentially no solvent derived residue that would interfere with metabolite analysis. It is also recognized that different times and temperatures may be used for the extraction of metabolites, including, but not limited to, transiently changing temperature such as may be achieved with microwaves. The method by which metabolites are extracted into solvent for analysis while retaining tissue and/or cell structures suitable for histological analysis is referred to as Solvent Extraction of Metabolites, or SEM.

IV. Histological Analysis

Preparation of a histologic section of a sample typically involves formalin fixation and processing of tissue using standard histological methods as described, for example, by Carson in *Histotechnology, A Self Instructional Text*. ASCP Press 1990. FIG. 1 provides a schematic representation of histological analysis using histologic sectioning of tissue specimens. Many of the steps described in FIG. 1 for paraffin-embedded tissue sections can be eliminated if a cryosection of tissue is prepared. In this situation, the cryosection is extracted and metabolites in the extract analyzed. In the current practice, where frozen sections are performed in real time for surgical consultations, the extract is discarded. Such cryosections are routinely fixed in alcohol, re-hydrated, and stained directly with hematoxylin and eosin for rapid turn-around times.

Preparation of cells for cytological analysis typically involves plating cells on a surface amenable to manual manipulation such as a glass coverslip or slide. The cells are then fixed using a precipitating fixative such as methanol. In the current routine practice, the extract is discarded and the cells are processed directly for immunocytochemistry.

V. Metabolomics

Metabolites may be detected using any suitable method including, but not limited to, liquid and gas phase chromatography, alone or coupled to mass spectrometry, NMR, immunoassays, chemical assays, spectroscopy and the like. For example, the methods described in U.S. Pat. Nos. 7,005,255; 7,329,489; 7,550,258; 7,550,260; 7,553,616; 7,635,556; 7,682,782; and 7,682,784 may be conducted using a small molecule profile obtained using the methods disclosed herein.

In other embodiments, metabolites are detected using optical imaging techniques such as magnetic resonance spectroscopy (MRS), magnetic resonance imaging (MRI), CAT scans, ultra sound, MS-based tissue imaging or X-ray detection methods.

VI. Compositions & Kits

Any of the methods, alone or in combination of the present invention, may be provided in the form of a kit. Kits may further comprise appropriate controls and/or detection reagents. In an embodiment, the kit may include tools and reagents for the analysis of a tissue sample or biopsy. The kit may comprise a sample collection element and a tool for placing the biopsy or tissue sample into the collection element. The collection element may contain extraction solvent, a tool to retrieve the tissue following incubation, and a tool to place the collected tissue sample into a collection receptacle for histological analyses. For example, the kit may comprise a sample collection element, an extraction solvent, a tissue retrieval element, a retrieved tissue collection receptacle, sample labels, sample barcodes, and instruction protocol. The instruction protocol may be provided as a printed form or booklet or on an electronic medium, such as, for example, a computer disk or other computer readable medium.

The kit may be used in accordance with the following exemplary method. A tissue sample may be removed from the tissue of interest using a biopsy needle. The tissue can then be extruded into a collection receptacle (e.g., a vial, a conical tube, etc.) containing an extraction solvent. Exemplary solvents include, but are not limited to, 80% methanol, 80% ethanol, or other solvents. The collection receptacle may then be incubated for a pre-determined period of time according to the method of the instant invention (e.g., 24 h at 22° C.-24° C.). Following incubation, the tissue sample may be removed using a tissue retrieval device (e.g., a spatula, a suction device, a forceps, etc.) and placed into a new collection receptacle (e.g., a vial, a test tube, a conical tube, etc.). The contents of the collection receptacle containing the extraction solvent may then be subjected to biochemical analysis while the contents of the collection receptacle containing the tissue sample may be subjected to histological analysis. Barcodes and labels enable the sample identity and the analyses results to be tracked through the biochemical and histological analyses.

Alternatively, the extraction solvent may be removed and placed in a new collection receptacle. The contents of the collection receptacle containing the tissue may then be subjected to histological analysis while the contents of the collection receptacle containing the extraction solvent may then be subjected to biochemical analysis.

The invention will be further explained with the following examples which are offered by illustration and not limitation.

EXAMPLES

I. General Methods
A. Identification of Metabolic Profiles

Each sample was analyzed to determine the concentration of several hundred metabolites. Analytical techniques such as GC-MS (gas chromatography-mass spectrometry) and LC-MS (liquid chromatography-mass spectrometry) were used to analyze the metabolites. Multiple aliquots were simultaneously, and in parallel, analyzed, and, after appropriate quality control (QC), the information derived from each analysis was recombined. Every sample was characterized according to several thousand characteristics, which ultimately amount to several hundred chemical species. The techniques used were able to identify novel and chemically unnamed compounds. The methods are described in US Patent Application Publication No. 2009/0179147; Evans et al., 2009, Analytical Chemistry 81: 6656-6667; and Lawton et al., 2008, Pharmacogenomics 9: 383-397.

B. Statistical Analysis

The metabolomic data can be analyzed using several statistical methods to identify molecules (either known, named metabolites or unnamed metabolites) present at differential levels in a definable population or subpopulation (e.g., biomarkers for cancer biological samples compared to non-cancer control biological samples) useful for distinguishing between the definable populations (e.g., cancer and control). Other molecules (either known, named metabolites or unnamed metabolites) in the definable population or subpopulation can also be identified.

Random forest analyses is used for classification of samples into groups (e.g. disease or healthy). Random forests give an estimate of how well individuals in a new data set can be classified into each group, in contrast to a t-test, which tests whether the unknown means for two populations are different or not. Random forests create a set of classification trees based on continual sampling of the experimental units and compounds. Then each observation is classified based on the majority votes from all the classification trees.

Regression analysis can be performed using the Random Forest Regression method and the Univariate Correlation/Linear Regression method to build models that are useful to identify the biomarker compounds that are associated with disease or disease indicators obtained from the histopathology report (e.g. tumor grade or tumor stage) and then to identify biomarker compounds useful to classify individuals. Biomarker compounds that are useful to predict disease or measures of disease (e.g. tumor grade) and that are positively or negatively correlated with disease or measures of disease (e.g. tumor grade) can be identified in these analyses.

Recursive partitioning relates a 'dependent' variable (Y) to a collection of independent ('predictor') variables (X) in order to uncover or understand the relationship, Y=f(X). This analysis can be performed with the JMP program (SAS) to generate a decision tree. The statistical significance of the "split" of the data can be placed on a more quantitative footing by computing p-values, which discern the quality of a split relative to a random event. The significance level of each "split" of data into the nodes or branches of the tree can be computed as p-values, which discern the quality of the split relative to a random event. It is given as LogWorth, which is the negative log 10 of a raw p-value.

Statistical analyses can be performed with the program "R" available on the worldwide web at the website cran.r-project.org and in JMP 6.0.2 (SAS® Institute, Cary, N.C.).

C. Histological Analysis

Figure 2:
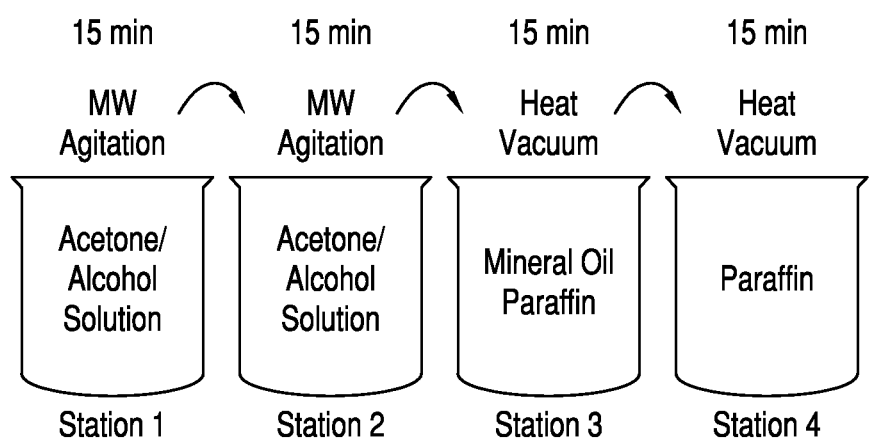
FIG. 2 provides a schematic illustration of histological processing of biopsy samples.

Biopsies were processed on a Tissue-Tek Xpress x50 (Sakura) following manufacturer's instructions with an approximate run time of 1.5 hrs. All processing reagents were purchased by Sakura (Sakura-Finetek, USA). A schematic illustration of the histological processing of the biopsy samples is shown in FIG. 2.

Sample Processing: The samples were processed as follows. At station 1, a sample was immersed and incubated in an acetone and alcohol solution at 40-44° C. and agitated continuously using 50 watts of microwave agitation for 15 minutes. At station 2, the sample was immersed and incubated in an acetone and alcohol solution at 40-44° C. and agitated continuously using 50 watts of microwave agitation for 15 minutes. At station 3, the sample was immersed and incubated at 64 to 66° C. in a mineral oil and paraffin mixture undergoing heat and vacuum for 15 minutes. At station 4, the sample was immersed and incubated in paraffin at 64 to 66° C. undergoing heat and vacuum for 15 minutes.

Embedding and Sectioning: The samples were embedded immediately following processing. The tissue was then sectioned by cutting thin sections from the paraffin blocks using a rotary microtome. The block was faced (i.e., paraffin was removed to expose the embedded tissue), then clamped into a rotary microtome, and then moved up and down advancing a set number of microns for cutting of sections. A layer of paper towel or gauze was spread over ice and a solution of ammonia water (900 mL dH2O plus 30 mL Ammonium Hydroxide) was poured over it to saturate the gauze. The block was then soaked on the ice/ammonia water for a minimum of 1 hour, making sure that the ice surface was smooth so that the entire block face was touching the ice/ammonia water evenly. No maximum time was determined; however less than 4 hours is recommended.

Figure 3:
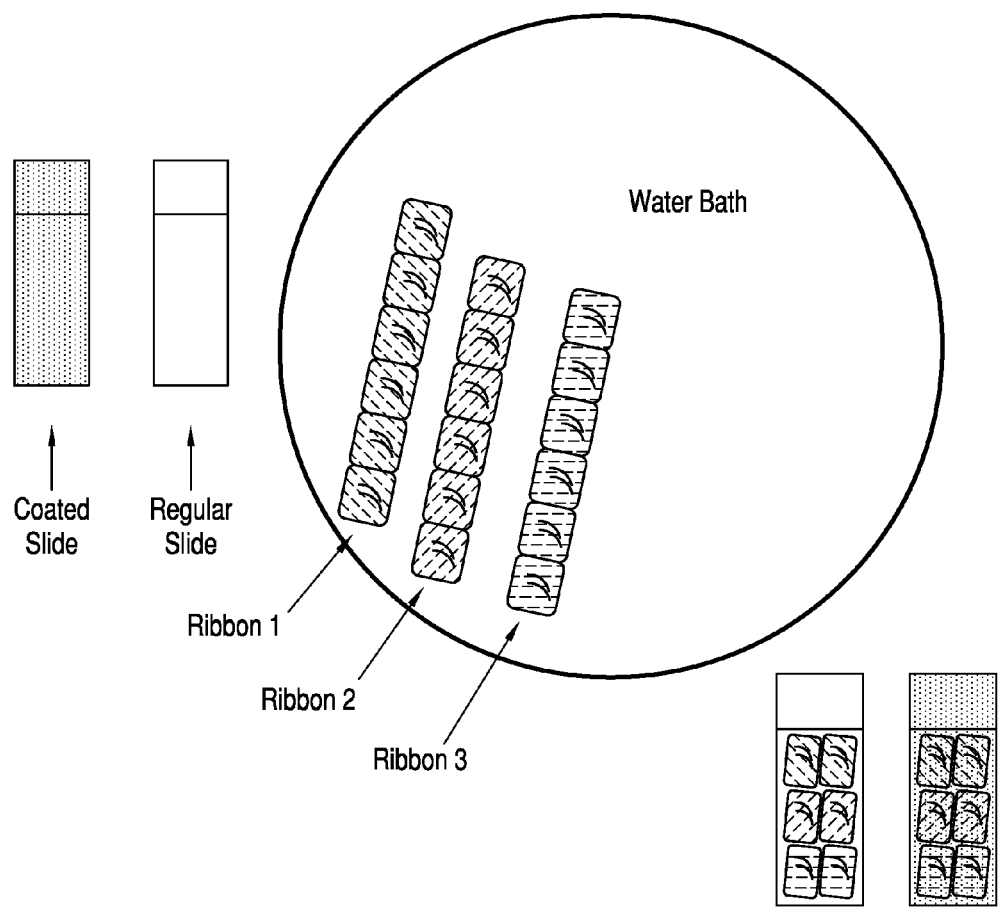
FIG. 3 illustrates a coated slide, a regular slide, ribbons floating on a water bath, and a completed slide with sections picked up from ribbon.

Prior to making sections of the core biopsies, coated slides and regular glass slides were prepared using standard slide preparation methods used in the art. Then, three ribbons of 3-4 sections each at 3-5 microns thickness were cut with the microtome. Each ribbon was floated on a water bath. One section from each ribbon was picked up per slide, beginning at the label on the slide. A schematic diagram is provided in FIG. 3.

Staining and Coverslipping: The slides containing paraffin sections were placed in a glass or metal slide holder, deparaffinized and rehydrated by incubating in a series of solutions. The slides were incubated in xylene for three minutes, and this was repeated twice, taking care to blot excess xylene from the slide before moving to the ethanol step. Then, the slides were placed in 100% ethanol for 3 minutes and this was repeated twice. Then, the slides were placed in 95% ethanol for 3 minutes. Then, the slides were placed in 80% ethanol for 3 minutes. Then, the slides were placed in deionized $H_2O$ for 5 minutes. While the sections were in water, the surface of hematoxylin stain solution was skimmed with a Kimwipe to remove oxidized particles. The excess water from the slide holder was blotted prior to placing the slide holder into the hematoxylin stain.

Hematoxylin staining: The slides were incubated in hematoxylin (Mayers Haematoxylin, filtered) for 3 minutes, then rinsed with deionized water. Then the slides were placed in tap water for 5 minutes to allow the stain to develop. Then the slides were dipped quickly 8-12 times in acid ethanol to destain. Next, the slides were rinsed twice for 1 minute each in tap water. Then, the slides were rinsed for 2 minutes in deionized water. Alternatively, the slides may remain overnight in the deionized water. Then, excess water was blotted from the slides prior to eosin staining.

Eosin staining and dehydration: The slides were incubated for 30 seconds in Eosin stain solution (Eosin Yellowish 1.0 g, 100 mL distilled H2O). Then, the slides were incubated three times for 5 minutes each in 95% ethanol. Then, the slides were incubated three times for 5 minutes each in 100% ethanol and the excess ethanol was blotted before placing the slides into the xylene. Then, the slides were incubated three times for 15 minutes each in xylene. Alternatively, the slides remained in xylene overnight to get good clearing of any water. Then, coverslips were placed on the slide using Permount. A drop of Permount was placed on the slide using a glass rod, taking care to leave no bubbles. The coverslip was then angled on the slide and allowed to fall gently onto the slide. The Permount was allowed to spread beneath the coverslip, covering all the tissue. The slides were then dried.

Example 1

Metabolite Extraction and Metabolomics Analysis of Prostate Tissue

Human non-cancerous prostate was cut into 10 mg tissue pieces and the pieces separately were placed into 15 ml polypropylene tubes (Fisher), 3 tissue pieces were individually extracted and analyzed for each method. Five ml of an aqueous solution of either 70% methanol or 70% ethanol were added to the tissue pieces and the immersed tissues were incubated for 24 hours at room temperature (between 22 and 24° C.). The method by which metabolites are extracted into solvent for analysis is referred to as Solvent Extraction of Metabolites, or SEM. The tissues were then removed from the solvents. The solvent extracts were evaporated to dryness under a stream of nitrogen gas at 40° C. in a Turbovap LV evaporator (Zymark). The dried extracts were reconstituted in 0.550 ml methanol/water (80:20), containing internal standards (D,L-fluorophenylglycine, D,L-4-chlorophenylalanine, tridecanoic acid, cholesterol-$D_6$). The reconstituted solution was analyzed by metabolomics as described in the general methods section above.

In order to compare the SEM method with the current state of the art method, human prostate tissue was also processed using the standard method that includes a tissue grinding step, and is thus destructive to the tissue. Approximately 50-100 mg of human non-cancerous prostate tissue was placed into a tube with 0.04 ml water per mg wet weight tissue, resulting in a tissue concentration of 200 mg of tissue per ml water, then homogenized by grinding in a 2 ml cryovial (Wheaton) in a Geno-grinder 2000 (SPEX). The concentration of the ground extract was adjusted by adding water, to be equivalent to 40 mg of initial wet weight of tissue per ml of water extract. A volume of 0.1 ml (4 mg tissue equivalent) of the reconstituted solution was analyzed by metabolomics as described in the General Methods section.

The metabolites recovered from the two methods, SEM and grinding were analyzed by high performance liquid chromatography/tandem mass spectrometry and gas chromatography/mass spectrometry as described above. The number of compounds that could be positively identified as known biochemicals based upon comparison with a chemical library of authentic chemical standards were 139 for the SEM method and 137 for the grinding method (see Table 1), demonstrating that SEM can be successfully employed for the extraction, recovery, and analysis of a plurality of metabolites. The ethanol and the methanol extracts performed similarly.

The number and identity of the metabolites detected using SEM are similar to those obtained with the currently used standard extraction method (i.e., over 70% of the same compounds were detected using both extraction methods). Thus, while the compounds detected were not identical, there was an over 70% overlap in the compounds detected. Some of the biochemicals detected by one method or the other were present in only a single sample and some were at the lower limits of detection. Without being bound by any theory, it is believed that the differences in the identity of the compounds detected using the different methods reflects biological variability and the small number of samples in the study. However, the same compound classes (e.g., sugars, amino acids, fatty acids, nucleotides, bile acids, lipids, etc.) were detected using both methods. Thus, the methods were not biased toward certain classes of compounds but instead were useful to detect a broad range of biochemicals.

TABLE 1

Comparison of the number of metabolites detected using SEM or standard, destructive tissue grinding method.

| Method | Number of Named Compounds |
| --- | --- |
| SEM | 139 |
| Grinding | 137 |

Example 2

Extraction of Metabolites, Metabolomics Analysis, and Histological Analysis of Tissue Specimens Post-operative needle biopsies of human prostate tissue were obtained from prostatectomy tissues. After weighing and measuring the prostate, prior to inking, the prostate was oriented posterior surface upwards and the apex oriented downward and the base upward. An 18 gauge biopsy gun was then used to acquire 12 cores distributed in a fashion which mimics that utilized for in vivo ultrasound directed core biopsies (one each as left apex lateral, left apex transition, left mid lateral, left mid transition, left base lateral, and left base transition; the process is repeated for the right prostate). Biopsies were immediately placed separately into polypropylene tubes (1 biopsy/tube) containing 2.5 ml of an aqueous solution of either 70% methanol or 70% ethanol and incubated for 24 hours at room temperature (between 22 and 24° C.). After 24 hrs incubation, the needle biopsies were placed in biopsy bags and cassettes which were then transferred to Molecular Fixative (UMFix, Sakura) until processed for histology as described below and the solvent extracts were subjected to metabolomic analysis using the methods described above. An accession number was assigned to each individual tissue specimen and extract to track matched tissue and extract samples.

The solvent extracts were transferred to 12×75 mm polypropylene tubes (Fisher) and evaporated to dryness under a stream of nitrogen gas at 40° C. in a Turbovap LV evaporator (Zymark). The dried extracts were reconstituted in 0.550 ml methanol/water (80:20), containing internal standards (D,L-fluorophenylglycine, D,L-4-chlorophenylalanine, tridecanoic acid, cholesterol-$D_6$). The reconstituted solutions were analyzed by metabolomics as described above.

Figure 4:
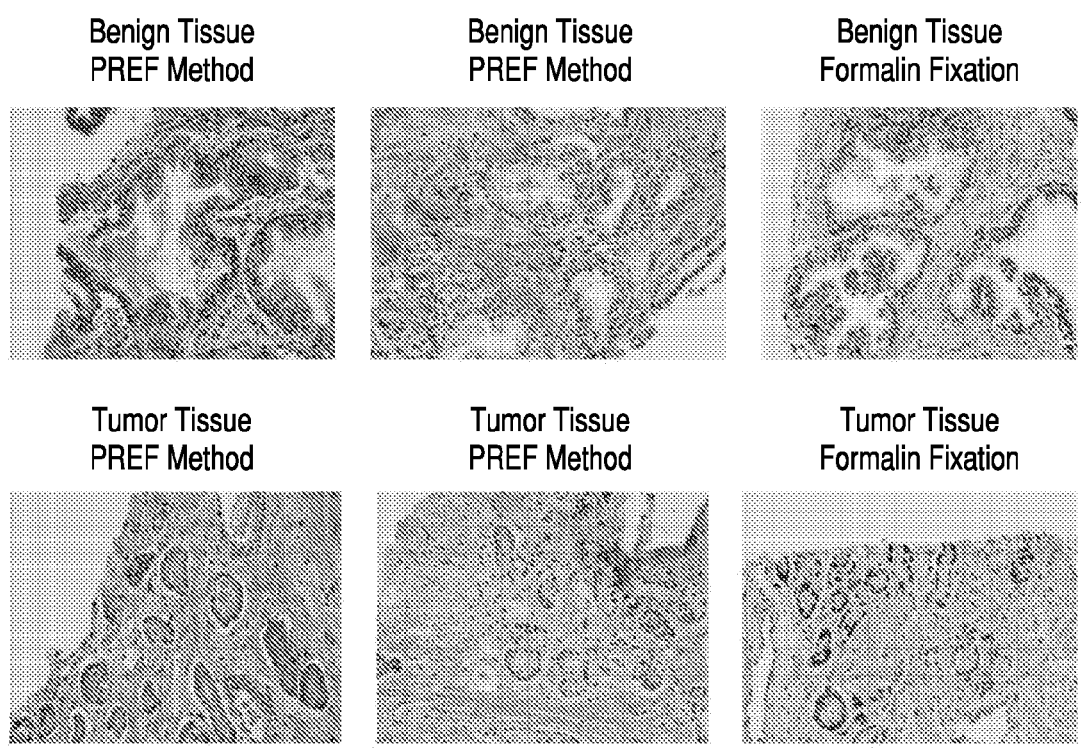
FIG. 4 illustrates histology of prostate biopsy tissues processed with the solvent extraction method and controls processed by a standard formalin method.

The combination of the SEM method for the extraction of metabolites coupled with histology is referred to as PReservation by Extraction and Fixation, abbreviated as PREF. Prostate biopsy specimens were successfully processed for histology, stained, and analyzed by a Board Certified pathologist after the SEM procedure was performed on the same specimens. FIG. 4 shows pictures of representative slides made from human prostate biopsy specimens that were processed according to the PREF method described herein, and, as controls, human prostate biopsy specimens that were processed according to the current state of the art formalin method. The results show that the cellular architecture has been well retained in the tissues processed using the PREF method. This result was observed for both non-cancer benign tissues and for cancer-containing tissues, as shown in FIG. 4.

Prostate biopsies were processed with either SEM fixation followed by H&E staining as described above in text, or with standard 10% neutral buffered formalin fixation followed by H&E staining. The pictures in FIG. 4 are pictures of histology slides from representative benign (non-tumor) biopsies, and from tumor containing biopsies. The top row of panels is benign tissue and the bottom row is tumor containing tissue. The solvent for SEM fixation for the upper left panel was 70% methanol. The solvent for SEM fixation for the upper middle panel was 70% ethanol; the specimen in the upper right panel was processed with the formalin method; the solvent for SEM fixation for the lower left panel was 70% ethanol; the solvent for SEM fixation for the lower middle panel was 70% methanol. The specimen in the lower right panel was processed with the formalin method.

Figure 5:
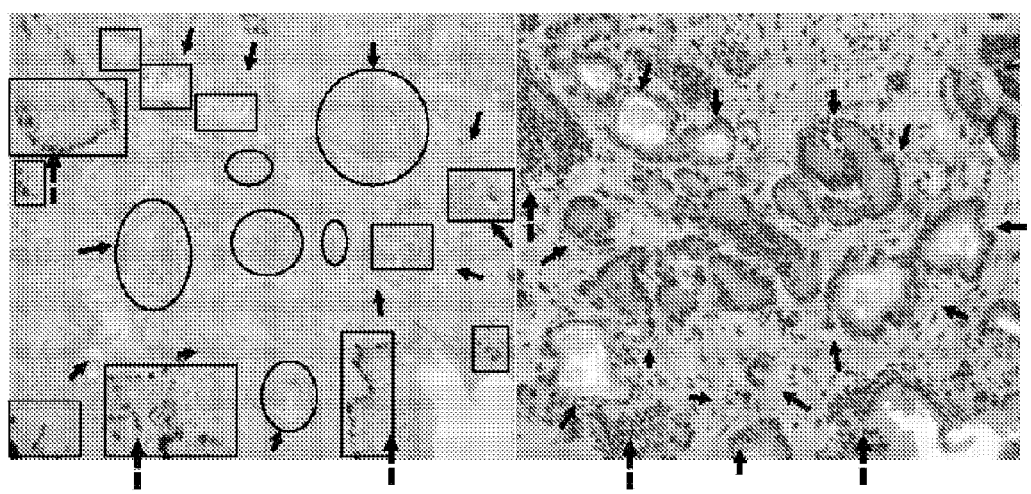
FIG. 5 illustrates immunohistochemistry (IHC) analysis following metabolite recovery.

In additional testing, it was determined that histological evaluation using immunohistochemical stains (IHC) can be performed following SEM fixation. Prostate biopsies were stained using PIN4 stain following SEM fixation. The pictures in FIG. 5 are photomicrographs of histology slides from representative tumor containing biopsies. The photos provide immunohistochemistry Analysis of biopsies following biochemical recovery. The results of the IHC stained section in FIG. 5 show that the PIN4 stain indicates racemase (circles, ovals) as well as p63 and basal keratin (rectangles) in SEM processed biopsies.

The left panel shows an IHC stained tissue section using PIN4 stain. The right panel shows an adjacent tissue section stained with hematoxylin and eosin (H & E). In FIG. 5, short arrows indicate prostatic adenomocarcinoma. Dashed arrows indicate benign glands. The rectangles indicate regions where PIN4 stain indicates p63 and basal keratin. The circles and ovals indicate regions where PIN4 stain indicates racemase. FIG. 5 shows that histological analysis using IHC and H&E staining may be performed following SEM fixation.

To determine if the SEM method was successful as performed on the identical samples that were analyzed by histology, the number of positively identified named biochemical compounds from the SEM extracts was determined by mass spectrometry (as described above). A total of 188 named biochemicals were observed and are listed in Table 2.

TABLE 2

Biochemicals Measured in Prostate Tissue Using SEM.

| | |
|---|---|
| 1-arachidonoylglycerophosphocholine | glutaroyl carnitine |
| 1-arachidonoylglycerophosphoethanolamine | glutathione, oxidized (GSSG) |
| 1-arachidonoylglycerophosphoinositol | glutathione, reduced (GSH) |
| 1-eicosadienoylglycerophosphocholine | glycerate |
| 1-eicosatrienoylglycerophosphocholine | glycerol |
| 1-heptadecanoylglycerophosphoethanolamine | glycerol 3-phosphate (G3P) |
| 1-linoleoylglycerophosphocholine | glycerophosphorylcholine (GPC) |
| 1-linoleoylglycerophosphoethanolamine | glycine |
| 1-methylnicotinamide | glycylleucine |
| 1-myristoylglycerophosphocholine | guanine |
| 1-oleoylglycerophosphocholine | guanosine |
| 1-oleoylglycerophosphoethanolamine | guanosine 5'-monophosphate (GMP) |
| 1-oleoylglycerophosphoinositol | heme |
| 1-palmitoleoylglycerophosphocholine | hexanoylcarnitine |
| 1-palmitoylglycerol (1-monopalmitin) | histamine |
| 1-palmitoylglycerophosphocholine | histidine |
| 1-palmitoylglycerophosphoethanolamine | homocarnosine |
| 1-palmitoylglycerophosphoinositol | hydroxyisovaleroyl carnitine |
| 1-stearoylglycerol (1-monostearin) | hypoxanthine |
| 1-stearoylglycerophosphocholine | inosine |
| 1-stearoylglycerophosphoethanolamine | inositol 1-phosphate (I1P) |
| 1-stearoylglycerophosphoinositol | isobutyrylcarnitine |
| 2-aminoadipate | isocitrate |
| 2-aminobutyrate | isoleucine |
| 2-arachidonoylglycerophosphocholine | isovalerylcarnitine |
| 2-arachidonoylglycerophosphoethanolamine | kynurenine |
| 2-docosahexaenoylglycerophosphoethanolamine | lactate |
| 2-docosapentaenoylglycerophosphoethanolamine | laurate (12:0) |
| 2-hydroxybutyrate (AHB) | leucine |
| 2-hydroxypalmitate | lidocaine |
| 2-hydroxystearate | linoleate (18:2n6) |
| 2-methylbutyroylcarnitine | lysine |
| 2-oleoylglycerophosphocholine | malate |
| 2-oleoylglycerophosphoethanolamine | margarate (17:0) |
| 2-palmitoylglycerol (2-monopalmitin) | mead acid (20:3n9) |
| 2-palmitoylglycerophosphocholine | methionine |
| 2-palmitoylglycerophosphoethanolamine | methyl-alpha-glucopyranoside |
| 2-stearoylglycerol (2-monostearin) | methylphosphate |
| 2-stearoylglycerophosphocholine | myo-inositol |
| 3-(4-hydroxyphenyl)lactate | myristate (14:0) |
| 3-dehydrocarnitine | myristoleate (14:1n5) |
| 3-hydroxybutyrate (BHBA) | N-acetyl-aspartyl-glutamate (NAAG) |
| 3-indoxyl sulfate | N-acetylneuraminate |
| 4-androsten-3beta,17beta-diol disulfate 1 | N-ethylglycinexylidide |
| 5-methylthioadenosine (MTA) | nicotinamide |
| 5-oxoproline | nicotinamide adenine dinucleotide (NAD+) |
| acetylcarnitine | nicotinamide adenine dinucleotide reduced (NADH) |
| acetylcholine | nonadecanoate (19:0) |
| acetylphosphate | oleate (18:1n9) |
| adenine | oleoylcarnitine |
| adenosine | ophthalmate |
| adenosine 5'-diphosphate (ADP) | palmitate (16:0) |
| adenosine 5'-monophosphate (AMP) | palmitoleate (16:1n7) |
| alanine | palmitoyl sphingomyelin |
| alpha-tocopherol | pantothenate |
| arabonate | p-cresol sulfate |
| arachidate (20:0) | pelargonate (9:0) |
| arachidonate (20:4n6) | pentadecanoate (15:0) |
| aspartate | phenol sulfate |
| betaine | phenylacetylglutamine |
| butyrylcarnitine | phenylalanine |
| carnitine | phosphate |
| carnosine | phosphoethanolamine |
| C-glycosyltryptophan | pregnen-diol disulfate |
| cholesterol | proline |
| choline | pseudouridine |
| choline phosphate | putrescine |
| cis-aconitate | S-adenosylhomocysteine (SAH) |
| citrate | scyllo-inositol |

TABLE 2-continued

Biochemicals Measured in Prostate Tissue Using SEM.

| | |
|---|---|
| citrulline | serine |
| creatine | spermidine |
| creatinine | spermine |
| cysteine | sphingosine |
| cysteine-glutathione disulfide | stachydrine |
| cysteinylglycine | stearamide |
| cytidine | stearate (18:0) |
| cytidine 5'-diphosphocholine | stearoyl sphingomyelin |
| cytidine 5'-monophosphate (5'-CMP) | stearoylcarnitine |
| dehydroisoandrosterone sulfate (DHEA-S) | succinate |
| deoxycarnitine | succinylcarnitine |
| dihomo-linoleate (20:2n6) | taurine |
| dihomo-linolenate (20:3n3 or n6) | threonine |
| docosahexaenoate (DHA; 22:6n3) | triethyleneglycol |
| docosapentaenoate (n3 DPA; 22:5n3) | tryptophan |
| docosapentaenoate (n6 DPA; 22:5n6) | tryptophan betaine |
| eicosapentaenoate (EPA; 20:5n3) | tyrosine |
| eicosenoate (20:1n9 or 11) | uracil |
| ergothioneine | urate |
| ethanolamine | urea |
| flavin adenine dinucleotide (FAD) | uridine |
| glucose | uridine 5'-monophosphate (UMP) |
| glutamate | valine |
| glutamate, gamma-methyl ester | xanthine |
| glutamine | xanthosine |

These results show that metabolomics analysis can be performed using SEM in a manner non-destructive of the tissue, and that the resulting tissue specimens can be analyzed histopathologically, including traditional staining and IHC analyses.

Example 3

Application of PREF for the Determination of the Aggressiveness of Cancer in Biopsy Specimens One of the applications of PREF is the determination of the aggressiveness of cancer. Gleason scoring is a classification system in pathology. As such, it is subject to scoring differences depending on the person or group responsible for assigning the Gleason scores. It would be useful to augment the pathological evaluation of tissues with quantitative measures of the same tissues, for example by the determination of the level(s) of one or more biochemical biomarkers in a sample. In the case of prostate cancer, certain biochemicals have been shown to correlate with cancer progression. The measurement of these and other compounds can be of use in the determination of disease aggressiveness. Table 3 shows the results of the assessment of prostate cancer aggressiveness as analyzed using the PREF method for different prostate biopsies. A sub-set of metabolites observed to have more pronounced differences between more vs. less aggressive prostate cancer is shown. Some of these compounds have been described previously as being associated with prostate cancer and/or prostate cancer aggressiveness (see, e.g., PCT Patent Application Publication No. WO2008036691A2; U.S. patent application Ser. No. 12/441,945; PCT Patent Application Publication No. WO2009026152A1; and US Patent Application Publication No. 2009/0075284, Sreekumar et al., *Metabolic profiles delineate potential role for sarcosine in prostate cancer progression.* 2009, Nature 457: 910-915.).

The results are shown in Table 3. Comparison 1 compares tumor-containing biopsies from patients with more aggressive cancer and less aggressive cancer as determined by the histopathology. A cancer that had spread outside of the prostate capsule was deemed aggressive while a cancer that had not spread outside of the prostate capsule was deemed less aggressive. Comparison 2 was performed for tumor-containing biopsy specimens that were graded by histology as either Gleason 4+3=7 or Gleason 3+4=7. Although the grading of 4+3 is considered more aggressive than a grading of 3+4, these two classification scores are close, and could possibly be scored differently by different pathology groups. Distinguishing a grade of 3+4 from 4+3 allows a clinician to select the most appropriate course of treatment. Typically, tumors that are graded 4+3 are aggressively treated, while tumors graded 3+4 may be treated with 'watchful waiting'. Determining the treatment course is valuable because of the significant co-morbidities associated with aggressive treatment. Hence, with prostate cancer, sometimes removing a less aggressive tumor is more detrimental to a patient's health and well-being than leaving the less aggressive tumor in place and monitoring it. Comparison 3 compared tumor-containing biopsy specimens (Gleason 4+3) with non-tumor tissues obtained from the same subject. The results in all comparisons show that the PREF method adds additional quantitative information to the classification-based histology results. Thus, PREF can be helpful in differentiating between a grade of 3+4 and a grade of 4+3. Of particular note is the observation of a lower relative difference in amounts for the comparison of the tumor vs. no tumor for the patient with the more aggressive cancer. One interpretation of these results is that the metabolite analysis is detecting a cancer signal at an early stage before the cellular changes that lead to a change in a histology characterization are detectable. This indicates that the PREF method may detect cancer in a tissue by metabolomics before it is apparent by histopathology analysis.

TABLE 3

PREF method and analysis of prostate biopsy specimens

| | Histology | | Metabolite % change (metabolomics via SEM method) | | | | | | |
|---|---|---|---|---|---|---|---|---|---|
| Comparson | Histology Comparison | Histology Description | cis-aconitate | citrate | isobutyryl-carnitine | kynurenine | spermine | uracil | xanthosine |
| 1 | pT3 vs. pT2 | Non-organ confined disease vs. organ confined disease | −83% | −91% | 177% | 207% | −100% | 102% | 297% |
| 2 | Tumor GS4 + 3 vs. GS 3 + 4 | Specimen Gleason Grade 4 + 3 vs Gleason Grade 3 + 4 | −80% | −84% | 129% | 405% | −99% | 128% | 273% |
| 3 | Tumor vs. No Tumor GS 4 + 3 | Specimen tumor vs. no tumor for GS 4 + 3 | −73% | −80% | 103% | 87% | −99% | 58% | 166% |

Example 4

Metabolite Extraction and Analysis of Bone

Some tissue types are recalcitrant to grinding and metabolite extraction. For example, spinal discs are not amenable to grinding, extraction of biochemicals therefrom is difficult, and results are variable. Further, when the extracts are injected onto Gas Chromatography (GC) or Liquid Chromatography (LC) columns, the columns clog and must be changed, which is costly in terms of the column expense, and the time required to replace the column and to recalibrate the instrument.

To determine if the SEM method is useful with this type of tissue, spinal discs were placed separately into polypropylene tubes (1 biopsy/tube) containing 2.5 ml of an aqueous solution of 80% methanol and incubated for 24 hours at room temperature (between 22 and 24° C.). After incubation, the solvent extracts were subjected to metabolomic analysis using the methods described herein above. The results were similar to the conventionally prepared spinal discs in terms of the number and identity of the metabolites detected. Both methods identified about 70 metabolites, and there was greater than 95% overlap between the metabolites identified by the two methods. There was a significant operational advantage to the SEM method in that the columns did not clog or need replacement when running samples extracted using this method.

Example 5

Metabolite Extraction and Metabolomics Analysis of Bovine Liver

Figure 6:
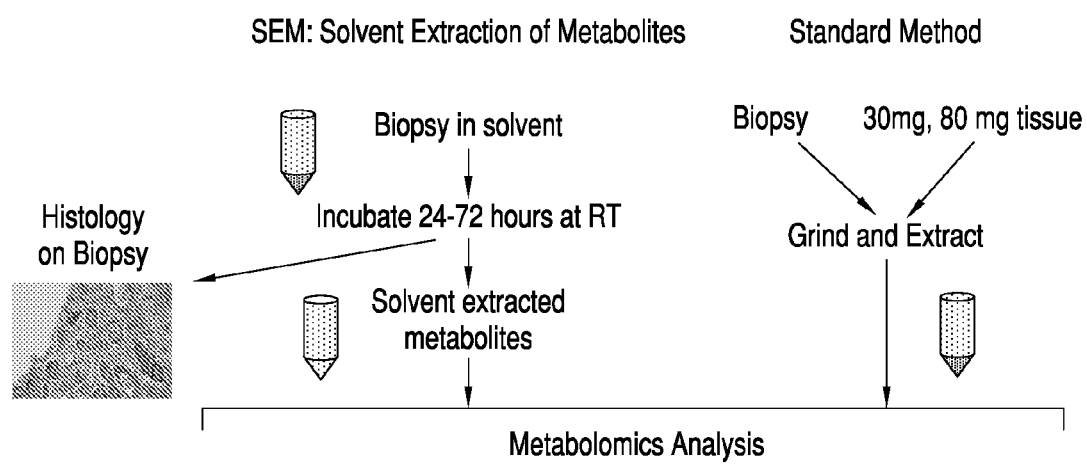
FIG. 6 illustrates the work flow of PREF and SEM compared to the work flow for the Standard Method for extracting metabolites for metabolomics.

To compare SEM with the current state of the art (standard) method of metabolite extraction from tissue, biopsy samples were obtained from bovine liver using an 18-gauge biopsy gun. FIG. 6 provides a schematic flowchart comparing PREF and SEM to the Standard Method which extracts metabolites for metabolomics but does not preserve tissue morphology or cellular architecture.

For SEM analysis, a single biopsy was placed in a Nalgene cryovial containing 2 ml of 80% MeOH and incubated for 24 hours at room temperature (22-24° C.). After a 5 minute spin at 2000 rpm, the solvent extract was transferred to a clean vial and evaporated to dryness under a stream of nitrogen gas at 40° C. in a Turbovap LV evaporator (Zymark). The dried extracts were reconstituted in 550 µl methanol:water (80:20) containing internal standards (D,L-2-fluorophenylglycine, D,L-4-chlorophenylalanine, tridecanoic acid, D6 cholesterol). The reconstituted solution was analyzed by metabolomics as described in Section I. A. of the General Methods section above.

For the current state of the art (standard) analysis, ~30 mg or ~80 mg pieces of bovine liver tissue or a bovine liver biopsy sample (obtained as described above) were processed using the standard method that includes a tissue grinding step, and is thus destructive to the tissue. The samples were placed in 2 mL Nalgene cryovials and 600 µl of 80% MeOH containing internal standards (D,L-2-fluorophenylglycine, D,L-4-chlorophenylalanine, tridecanoic acid, D6 cholesterol) was added to each vial. The tissues (biopsy, 30 mg piece, and 80 mg piece) were homogenized in a Geno-grinder 2000 (SPEX). The samples were spun for 1 min at 2000 rpm. For tissue pieces, the concentration of the ground extract was adjusted by adding 80% MeOH, to be equivalent to 40 mg of initial wet weight of tissue per ml of MeOH extract. For biopsies, the concentration of the ground extract was adjusted by adding 80% MeOH, to be equivalent to 7.7 mg of initial wet weight of tissue per ml of MeOH extract. Volumes of 550 µl (22 and 4.2 mg tissue equivalent for pieces and biopsies, respectively) of the reconstituted solution were analyzed by metabolomics as described in Section I. A. of the General Methods section.

The number of compounds for each method that could be positively identified as known biochemicals based upon comparison with a chemical library of authentic chemical standards is presented in Table 4. These results demonstrate that SEM can be successfully employed for the extraction, recovery, and analysis of a plurality of metabolites.

The metabolites that were identified in the samples are listed in Table 15. There is ~90% overlap in the identity of metabolites detected using SEM (the metabolites in the extract of a single 5 mg biopsy) compared to the standard method (extraction of 30 mg or 80 mg of tissue). These results indicate that the number and identity of metabolites obtained with SEM are equivalent to those obtained with the standard method.

TABLE 4

Comparison of the number of metabolites detected using SEM versus the Standard Method.

| | 30 mg tissue (Standard Method) | 80 mg tissue (Standard Method) | Biopsy (Standard Method) | Biopsy (SEM) |
|---|---|---|---|---|
| Total named metabolites | 240 | 240 | 229 | 211 |
| Not detected | 0 | 0 | 11 | 29 |

To compare solvent extraction conditions the following conditions were tested: 80% vs. 70% methanol, and incubation with shaking compared to stationary incubation. Biopsy samples were obtained from bovine liver using an 18-gauge biopsy gun. As a control for the standard method of metabolite extraction from tissue, ~30 mg pieces of bovine liver tissue or a bovine liver biopsy sample (obtained as described above) were processed using the standard method that includes a tissue grinding step, and is thus destructive to the tissue. The samples were placed in 2 mL Nalgene cryovials, and 600 µl of MeOH containing internal standards (D,L-2-fluorophenylglycine, D,L-4-chlorophenylalanine, tridecanoic acid, D6 cholesterol) was added to each vial. The tissues (biopsy, 30 mg piece) were homogenized in a Genogrinder 2000 (SPEX). The samples were spun for 1 min at 2000 rpm. The concentration of the ground extract was adjusted by adding MeOH as described earlier in this example. For SEM analysis, a single biopsy was placed in a Nalgene cryovial containing 2 ml of 80% MeOH and incubated for 24 hours at room temperature (22-24° C.). After a 5 minute spin at 2000 rpm, the solvent extract was transferred to a clean vial and evaporated to dryness under a stream of nitrogen gas at 40° C. in a Turbovap LV evaporator (Zymark). The dried extracts were reconstituted in 550 µl methanol:water (80:20) containing internal standards (D,L-2-fluorophenylglycine, D,L-4-chlorophenylalanine, tridecanoic acid, D6 cholesterol). Volumes of 550 µl for all samples were analyzed by metabolomics as described in Section I.A. of the General Methods section. The number of compounds identified based on comparison to a chemical library of authentic standards for each method is shown in Table 5. Each method (70% or 80% MeOH, incubation with shaking or stationary incubation) yielded essentially the same number, identity, and amount of metabolites demonstrating that SEM is a robust method for metabolite extraction using a broad range of acceptable conditions.

between prostates with aggressive cancer tumors and prostates with less aggressive cancer tumors based upon clinical histopathological staging.

Post-operative needle biopsies of human prostate tissue were obtained using an 18 gauge biopsy gun and placed into cryovials (Nalgene) containing 2 ml of 80% methanol. A single biopsy was placed in each vial and incubated for 24 hours at room temperature (22-24° C.). Following incubation, the tissues were removed from the solvent for histological analysis, and the solvent was prepared for metabolomics analysis.

For histopathology, after incubation, each biopsy was placed in a biopsy bag and cassette which was transferred to Molecular Fixative (UMFix, Sakura) until processed for histology as described in the histological analysis section of general methods and in Example 2. A Board-Certified pathologist analyzed the samples. Cellular architecture was well retained in the tissues processed using PREF. Each sample was classified as positive or negative for cancer and could be staged as T2 or T3. Seven biopsy samples that were classified as stage T2 and seven biopsy samples classified as stage T3 were selected for analysis using SEM.

For metabolomics analysis, the solvent extracts were evaporated to dryness under a stream of nitrogen gas at 40° C. in a Turbovap LV evaporator (Zymark). The dried extracts were reconstituted in 550 µl methanol:water (80:20) containing recovery standards (D,L-2-fluorophenylglycine, D,L-4-chlorophenylalanine, tridecanoic acid, D6 cholesterol). The reconstituted solution was analyzed by metabolomics as described in the general methods section above. A total of 260 named biochemicals were identified in the extract using SEM. The identified metabolites are listed in Table 15.

Statistical analysis was performed to identify metabolites that are significantly altered in the extracts from tumor-containing compared to the benign samples. The results of the t-test analysis showed that 83 metabolites were significantly ($p<0.05$) altered in the 14 sample extracts from prostate cancer biopsies compared to the 14 extracts from benign (non-cancer) biopsy samples. A list of these biochemicals with fold change values is shown in Table 6.

TABLE 5

Number of metabolites detected using various SEM extraction conditions.

| | Experimental Conditions | | | | | | |
|---|---|---|---|---|---|---|---|
| | 30 mg Tissue CONTROL Standard Method | 70% MeOH Biopsy (Standard method) | 80% MeOH Biopsy (Standard method) | 70% MeOH Shaking SEM Biopsy | 80% MeOH Shaking SEM Biopsy | 70% MeOH Stationary SEM Biopsy | 80% MeOH Stationary SEM Biopsy |
| Total Named Metabolites | 229 | 217 | 224 | 229 | 230 | 229 | 229 |

Example 6

PREF Analysis of Prostate Biopsies to Determine Presence of and Aggressiveness of Prostate Cancer The PREF method was performed on patient tissue samples obtained following prostatectomy. Based on histopathology analysis, eight cancer tumor positive and patient-matched benign (non-cancer) samples were selected from patients with stage T2 prostate cancer, and eight cancer tumor positive and matched benign samples were selected from patients with stage T3 prostate cancer. This experimental design allowed the determination of metabolite differences between cancer tumor-containing and benign regions of the prostate as well as the determination of metabolite differences

TABLE 6

Metabolites altered in prostate cancer-positive biopsy samples.

| BIOCHEMICAL NAME | Tumor Benign |
|---|---|
| N-acetylaspartate (NAA) | 6.07 |
| N-acetylglucosamine | 5.92 |
| xanthine | 5.24 |
| dihomo-linoleate (20:2n6) | 4.76 |
| cysteine | 4.64 |

TABLE 6-continued

Metabolites altered in prostate cancer-positive biopsy samples.

| BIOCHEMICAL NAME | Tumor Benign |
|---|---|
| docosapentaenoate (n6 DPA; 22:5n6) | 4.17 |
| 1-stearoylglycerophoinositol | 4.03 |
| uracil | 4.01 |
| 1-oleoylglycerophoinositol | 3.71 |
| methionine | 3.62 |
| ethanolamine | 3.44 |
| cysteine-glutathione disulfide | 3.39 |
| 1-palmitoylglycerophoinositol | 3.35 |
| gamma-glutamylglutamine | 3.29 |
| docosahexaenoate (DHA; 22:6n3) | 3.24 |
| eicosenoate (20:1n9 or 11) | 2.97 |
| cystine | 2.87 |
| 10-nonadecenoate (19:1n9) | 2.84 |
| ribose | 2.74 |
| ornithine | 2.70 |
| 1-oleoylglycerophoserine | 2.61 |
| 1-linoleoylglycerophoethanolamine | 2.60 |
| glycine | 2.59 |
| 1-oleoylglycerophoethanolamine | 2.40 |
| 2-oleoylglycerophoethanolamine | 2.39 |
| glutamate | 2.37 |
| pantothenate | 2.35 |
| lysine | 2.32 |
| betaine | 2.32 |
| gamma-glutamylglutamate | 2.28 |
| 1-stearoylglycerophoethanolamine | 2.22 |
| aspartate | 2.21 |
| 1-arachidonoylglycerophoinositol | 2.20 |
| methylphosphate | 2.20 |
| hypoxanthine | 2.18 |
| alpha-tocopherol | 2.16 |
| succinylcarnitine | 2.16 |
| glycerol 2-phosphate | 2.14 |
| oleate (18:1n9) | 2.13 |
| 2-palmitoylglycerophoethanolamine | 2.12 |
| serine | 2.12 |
| fumarate | 2.09 |
| 4-hydroxybutyrate (GHB) | 2.08 |
| trans-4-hydroxyproline | 2.07 |
| 2-aminoadipate | 2.06 |
| malate | 2.03 |
| xanthosine | 1.97 |
| propionylcarnitine | 1.96 |
| tryptophan | 1.95 |
| 1-arachidonoylglycerophoethanolamine | 1.93 |
| cytidine | 1.92 |
| butyrylcarnitine | 1.91 |
| N-acetyl-aspartyl-glutamate (NAAG) | 1.90 |
| 5-oxoproline | 1.89 |
| tyrosine | 1.87 |
| uridine | 1.86 |
| 3-dehydrocarnitine | 1.86 |
| glycerol | 1.86 |
| adenine | 1.81 |
| phenylalanine | 1.81 |
| glycerophosphorylcholine (GPC) | 1.80 |
| isoleucine | 1.79 |
| 2-aminobutyrate | 1.79 |
| leucine | 1.76 |
| choline | 1.71 |
| myristoleate (14:1n5) | 1.70 |
| carnitine | 1.69 |
| deoxycarnitine | 1.64 |
| guanosine | 1.63 |
| succinate | 1.62 |
| proline | 1.61 |
| inosine | 1.61 |
| valine | 1.60 |
| acetylcarnitine | 1.60 |
| S-adenosylhomocysteine (SAH) | 1.57 |
| alanine | 1.56 |
| histidine | 1.55 |
| benzoate | 1.42 |
| threonine | 1.41 |
| pseudouridine | 1.26 |
| caprylate (8:0) | 1.21 |
| arginine | 1.18 |
| glucose 1-phosphate | 0.70 |

Random forest analysis was used to classify samples into cancer positive or cancer negative groups. Random forests give an estimate of how well individuals in a new data set can be classified into each group. This is in contrast to a t-test, which tests whether or not the unknown means for two populations are different. Random forests create a set of classification trees based on continual sampling of the experimental units and compounds. Then each observation is classified based on the majority votes from all the classification trees.

Random forest results show that the samples can be classified correctly between cancer positive and cancer negative with 81% prediction accuracy. Table 7 provides a confusion matrix, which demonstrates that by using PREF prostate extracts, cancer-negative samples can be distinguished from cancer-positive samples. The "Out-of-Bag" (OOB) Error rate gives an estimate of how accurately new observations can be predicted using the random forest model (e.g., whether a sample contains tumor (cancer-positive) or is benign (cancer-negative)).

TABLE 7

Confusion Matrix showing that cancer-positive and cancer-negative prostate samples can be distinguished from each other.
Confusion Matrix: Benign (cancer-negative) vs. Tumor (cancer-positive)

| | Cancer-negative (Predicted) | Cancer-positive (Predicted) | Error |
|---|---|---|---|
| Cancer-negative (Actual) | 7 | 1 | 12.50% |
| Cancer-positive (Actual) | 2 | 6 | 25% |

OOB error 19%

Figure 7:
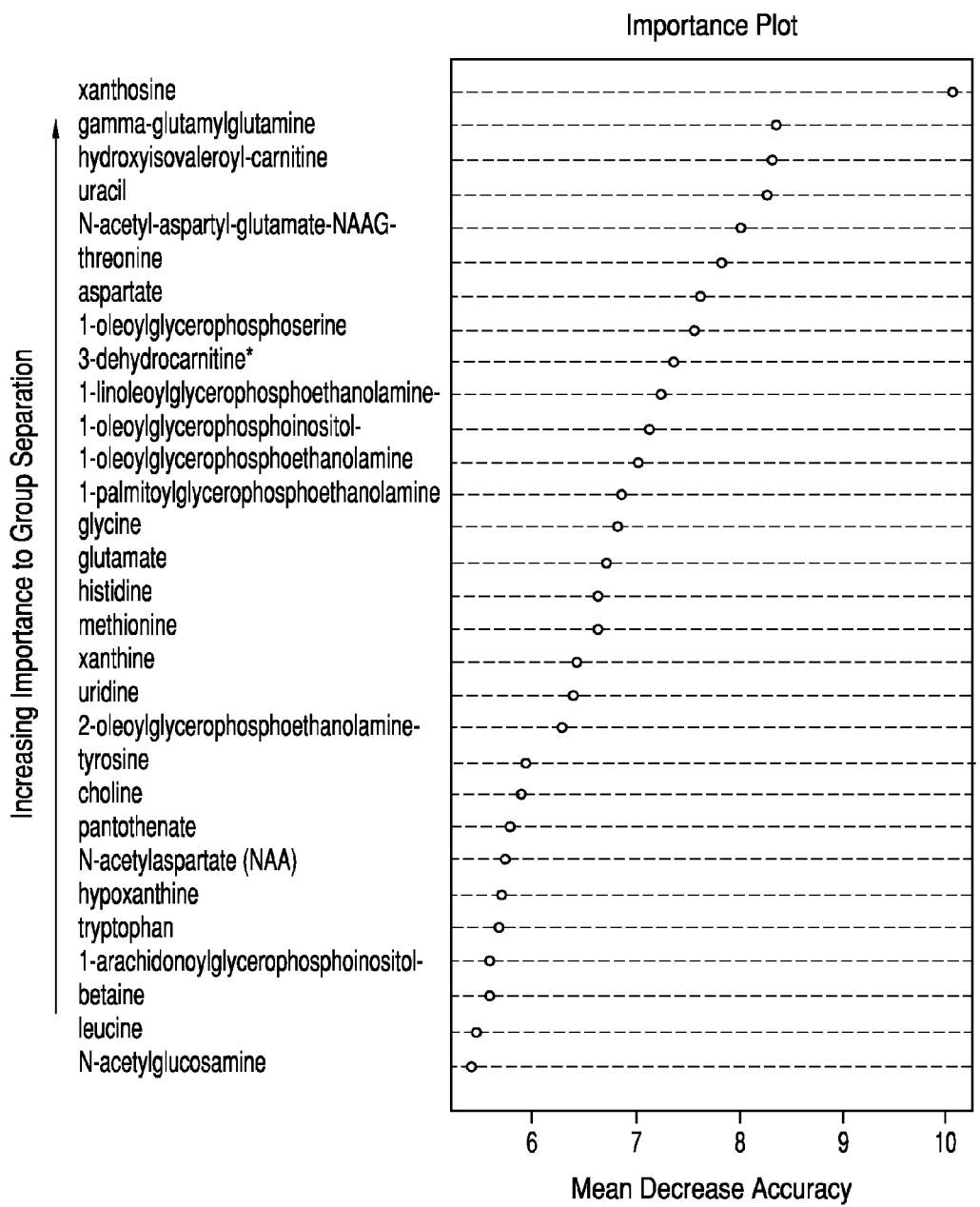
FIG. 7 illustrates a Random Forest Importance Plot for biomarkers useful to distinguish prostate cancer positive from cancer negative tumors as described in Example 6.

Based on the OOB Error rate of 19%, the Random Forest model that was created can be used to predict whether a sample has cancerous tumor or not with about 81% accuracy from analysis of the levels of the biomarkers in samples from the subject and a sensitivity of approximately 88% and a specificity of approximately 75%. The Random Forest model was used to create an importance plot, which indicates the biomarkers that are the most important biomarkers for distinguishing between cancer and non-cancer. FIG. 7 is an illustration of the importance plot created by the Random Forest model.

The samples were also analyzed to determine if PREF is useful to distinguish metabolites that are altered in more aggressive (T3) compared to less aggressive (T2) cancer. Statistical analysis was performed to identify metabolites that are significantly altered in the extracts from the seven T3 cancer samples compared to the seven T2 cancer samples. The results of the t-test analysis showed that a subset of metabolites had altered levels (p<0.05) in more aggressive (T3) compared to less aggressive (T2) prostate cancer. These metabolites and the fold-change observed are listed in Table 8.

TABLE 8

Metabolites altered in more aggressive prostate cancer.

| BIOCHEMICAL NAME | Less aggressive More aggressive |
|---|---|
| putrescine | 10.16 |
| spermine | 6.28 |
| agmatine | 5.62 |
| N-acetylputrescine | 2.78 |
| nicotinamide adenine dinucleotide reduced (NADH) | 2.77 |
| acetylcholine | 2.67 |
| spermidine | 2.07 |
| pyroglutamine | 2.04 |
| 1-methylnicotinamide | 0.57 |
| 2-methylbutyroylcarnitine | 0.53 |
| glycolate (hydroxyacetate) | 0.51 |
| 5-oxoproline | 0.43 |
| cysteine | 0.30 |

Example 7

PREF Analysis of Kidney Biopsies to Determine the Presence of Renal Cancer

The PREF method was performed on tissue obtained from post-nephrectomy biopsy samples. Based on histopathology analysis, six cancer tumor positive and six patient-matched benign (non-cancer) samples were selected from patients with kidney cancer. This experimental design allowed the determination of metabolite differences between cancer tumor-containing and benign regions of the kidney.

Human kidney core biopsies were obtained using a biopsy gun and placed into cryovials (Nalgene) containing 2 ml of 80% methanol. A single biopsy was placed in each vial and incubated for 24-72 hours at room temperature (22-24° C.). Following incubation, the tissues were removed from the solvent for histological analysis, and the solvent was prepared for metabolomics analysis.

For histopathology, after incubation, each biopsy was placed in a biopsy bag and cassette which was transferred to Molecular Fixative (UMFix, Sakura) until processed for histology as described in the histological analysis section of general methods and in Example 2. A Board-Certified pathologist analyzed the samples. Cellular architecture was well retained in the tissues processed using PREF, allowing for selection of samples containing cancer tumors and benign (non-cancer) samples.

For metabolomics analysis, the solvent extracts were evaporated to dryness under a stream of nitrogen gas at 40° C. in a Turbovap LV evaporator (Zymark). The dried extracts were reconstituted in 550 μl methanol:water (80:20) containing recovery standards (D,L-2-fluorophenylglycine, D,L-4-chlorophenylalanine, tridecanoic acid, D6 cholesterol). The reconstituted solution was analyzed by metabolomics as described in the general methods section above. A total of 218 named biochemicals were identified in the extract using SEM and are presented in the list in Table 15.

Statistical analysis was performed to identify metabolites that are significantly altered in the extracts from cancer tumor-containing compared to the benign (non-cancer) samples. The results of the t-test analysis showed that 69 metabolites were significantly ($p<0.05$) altered in the extracts from cancer tumor-containing kidney biopsies compared to the extracts from benign biopsy samples. A list of these biochemicals with fold change values is presented in Table 9.

TABLE 9

Metabolites altered in kidney cancer-positive biopsy samples.

| BIOCHEMICAL NAME | Positive/Negative |
|---|---|
| oleoylcarnitine | 12.34 |
| phosphoethanolamine | 8.79 |
| 2-arachidonoylglycerophosphoethanolamine | 8.31 |
| sphingosine | 8.16 |
| 2-arachidonoylglycerophosphocholine | 8.01 |
| stearoylcarnitine | 6.48 |
| 1-palmitoylglycerophosphocholine | 6.22 |
| 1-linoleoylglycerophosphocholine | 5.50 |
| glutathione, oxidized (GSSG) | 5.33 |
| pyruvate | 5.31 |
| 3-aminoisobutyrate | 5.18 |
| urea | 5.17 |
| 2-docosahexaenoylglycerophosphoethanolamine | 4.79 |
| 2-oleoylglycerophosphoethanolamine | 4.74 |
| N-acetylneuraminate | 4.65 |
| methyl-alpha-glucopyranoside | 4.54 |
| 2-palmitoylglycerophosphocholine | 4.42 |
| 2-oleoylglycerophosphocholine | 4.27 |
| malate | 4.21 |
| 1-oleoylglycerophosphocholine | 4.20 |
| 5-methylthioadenosine (MTA) | 3.70 |
| pyroglutamine | 3.55 |
| acetylcarnitine | 3.33 |
| succinate | 3.06 |
| 2-hydroxyglutarate | 3.05 |
| nicotinamide adenine dinucleotide (NAD+) | 2.88 |
| carnitine | 2.87 |
| deoxycarnitine | 2.86 |
| betaine | 2.75 |
| 3-dehydrocarnitine | 2.72 |
| alanine | 2.68 |
| butyrylcarnitine | 2.63 |
| 1-arachidonoylglycerophosphoinositol | 2.60 |
| glycerate | 2.39 |
| serine | 2.31 |
| 1-linoleoylglycerophosphoethanolamine | 2.28 |
| 2-docosahexaenoylglycerophosphocholine | 2.24 |
| Glycine | 2.14 |
| 1-arachidonoylglycerophosphocholine | 2.10 |
| proline | 2.07 |
| phosphate | 2.02 |
| adenine | 1.96 |
| 2-hydroxybutyrate (AHB) | 1.93 |
| lactate | 1.89 |
| 3-hydroxybutyrate (BHBA) | 1.85 |
| 5,6-dihydrouracil | 1.84 |
| stachydrine | 1.82 |
| hexanoylcarnitine | 1.79 |
| cholesterol | 1.75 |
| ornithine | 1.73 |
| 2-aminobutyrate | 1.66 |
| uridine | 1.60 |
| glycerol | 1.60 |
| threonine | 1.58 |
| tryptophan | 1.56 |
| isoleucine | 1.56 |
| tyrosine | 1.55 |
| margarate (17:0) | 1.54 |
| phenylalanine | 1.50 |
| leucine | 1.48 |
| phosphoglycerate (2 or 3) | 1.43 |
| histidine | 1.41 |
| 5-oxoproline | 1.41 |
| glutamine | 1.40 |
| lysine | 1.38 |
| stearate (18:0) | 1.38 |
| valine | 1.36 |
| arginine | 1.26 |
| palmitate (16:0) | 1.25 |

Random forest analysis was used to classify kidney samples into cancer positive or cancer negative groups.

Random forest results show that the samples can be classified correctly with 83% prediction accuracy. Table 10 provides a confusion matrix demonstrating that by using PREF kidney extracts, cancer-negative samples can be distinguished from cancer-positive samples. The "Out-of-Bag" (OOB) Error rate gives an estimate of how accurately new observations can be predicted using the random forest model (e.g., whether a sample contains tumor (cancer-positive) or is benign (cancer-negative)).

TABLE 10

Confusion Matrix showing that cancer-positive and cancer-negative kidney samples can be distinguished from each other.
Confusion Matrix: Benign (cancer-negative) vs. Tumor (cancer-positive)

|  | Cancer-negative Predicted | Cancer-positive Predicted | Error |
|---|---|---|---|
| Cancer-negative Actual | 6 | 0 | 0.00% |
| Cancer-positive Actual | 2 | 4 | 33% |

Out of bag error 17%

Figure 8:
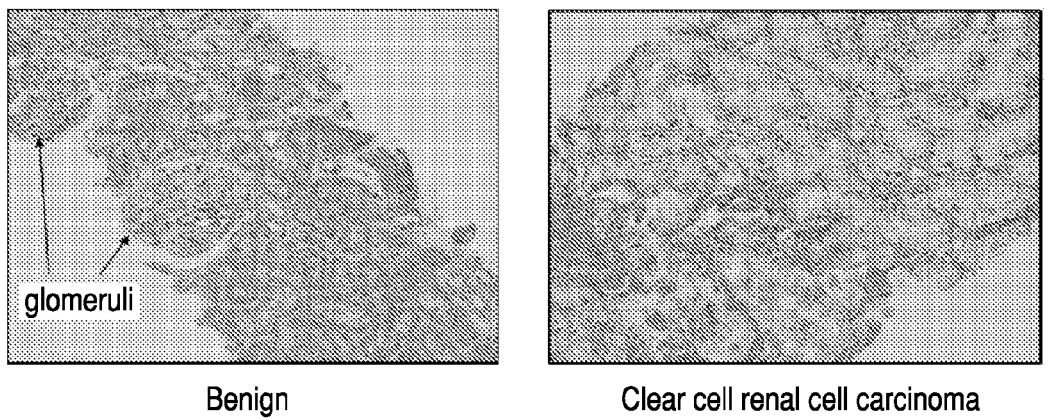
FIG. 8 illustrates histology of kidney biopsy tissues processed with the PREF method as described in Example 7.
Figure 9:
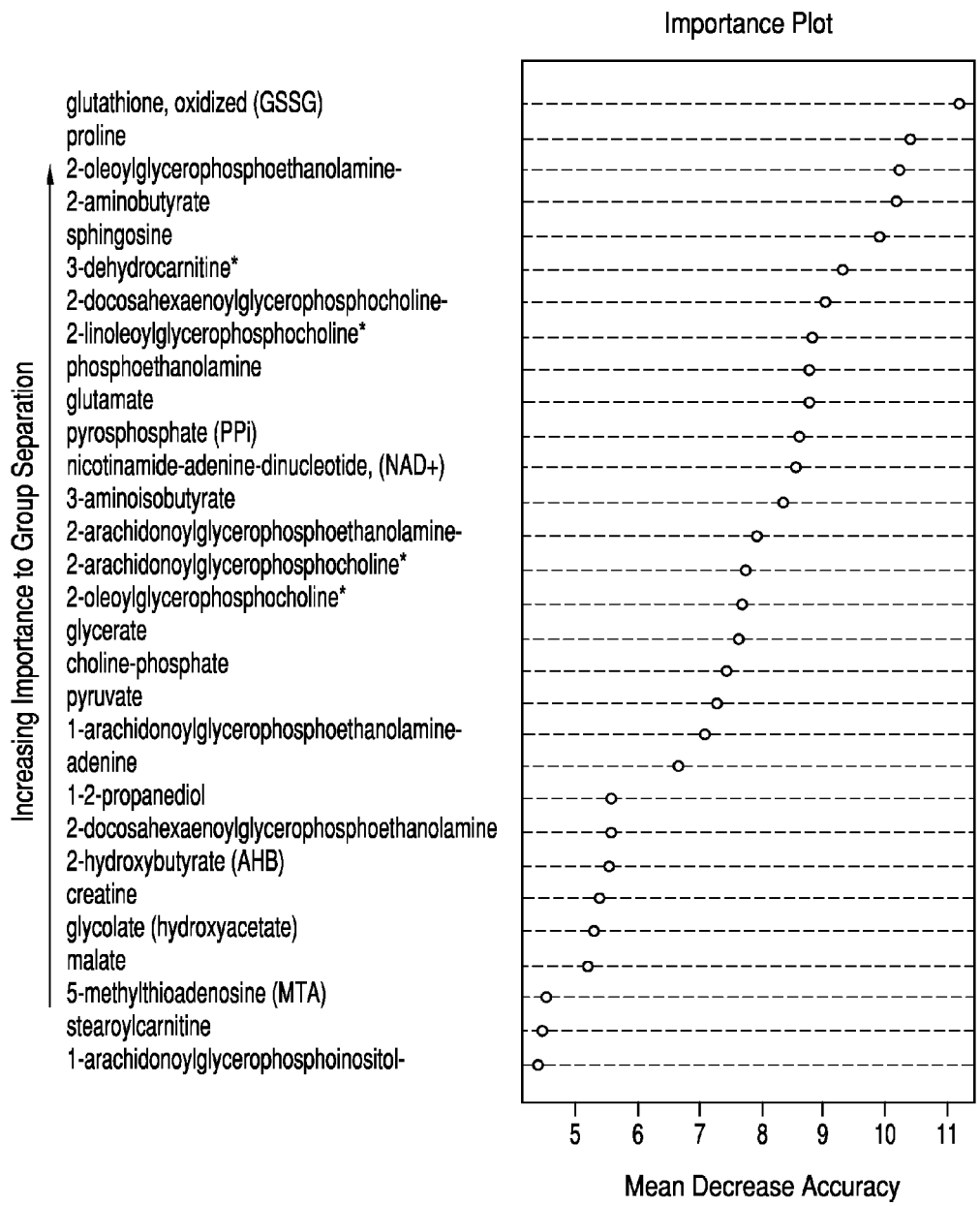
FIG. 9 illustrates a Random Forest Importance Plot for biomarkers useful to distinguish kidney cancer-positive from cancer-negative tumors as described in Example 7.

Based on the OOB Error rate of 17%, the Random Forest model that was created can be used to predict whether a sample has cancerous tumor or not with about 83% accuracy from analysis of the levels of the biomarkers in samples from the subject. The Random Forest model was used to create an importance plot for the groups in Example 7, which is shown in FIG. 8.

Example 8

Extraction of Metabolites and Metabolomics Analysis of Cultured Cells

The following example was performed to compare the results obtained using the PREF method to those obtained using standard methods. To determine the utility of PREF to study the biochemical changes in cultured cells, biochemicals were measured using methanol extract from human adherent cells, leaving the cells intact on the plate. As one of ordinary skill in the art will understand, the standard method of collecting samples of cells grown on a solid support requires scraping the cells from the culture vessels, which is time consuming, requires a centrifugation step and poses difficulty in standardizing the amount of time to collect each sample thereby introducing additional experimental variation into the collection process. In contrast, SEM does not require scraping and centrifugation. The absence of scraping and centrifugation saves time and allows faster sample processing, which combined with the immediate quenching of metabolism that results from the addition of the methanol or ethanol solvent, preserves the metabolic state of the cells and provides for a more accurate view of cell physiology. Additionally, metabolites may be detected at higher levels using SEM, which allows analysis of samples containing fewer cells and enables the use of smaller vessel sizes thereby further increasing the efficiency and processing capacity using SEM. Since SEM is non-destructive, the cells are available for immunocytochemical analysis.

For the SEM method, human embryonic kidney cells (HEK293) were grown to confluence in 6-well plates. Media was discarded, and all cells were quickly washed once with PBS which was subsequently discarded. An 80% room temperature methanol (20% water) solution was added to the cells, and the cells were incubated in the methanol solvent at room temperature for five minutes. After this incubation, the methanol solvent only (leaving cells attached to the plate) was transferred to a clean tube. The solvent extracts were evaporated to dryness under a stream of nitrogen gas at 40° C. in a Turbovap LV evaporator (Zymark). The dried extracts were reconstituted in 550 µl methanol:water (80:20) containing internal standards (D,L-2-fluorophenylglycine, D,L-4-chlorophenylalanine, tridecanoic acid, D6 cholesterol). The reconstituted solution was analyzed by metabolomics as described in the general methods section above.

In order to compare the SEM method with the current sample preparation method in which the cells are scraped and then homogenized, another plate of HEK293 cells was processed simultaneously with the above plate using the standard method and metabolomically analyzed. For the standard method, cells were rinsed quickly with PBS as above. A rubber policeman was used to dislodge cells, and cells were transferred to a clean tube. Cells were spun twice at 1000 g for 1 min, and supernatant was removed after each spin. 125 µl of water was added to each pellet and mixed by trituration. 450 µl of methanol:water (80:20) containing internal standards were added to 100 µl of each sample. Samples were homogenized by shaking in a Geno-grinder 2000 (SPEX).

The metabolites recovered using SEM and the standard method were analyzed by high performance liquid chromatography/tandem mass spectrometry and gas chromatography/mass spectrometry as described above. The number of biochemicals identified as matching to chemical standards in a chemical library were 236 for SEM and 172 for the standard method using cell scraping and homogenization (see Table 11). Sixty-six of the metabolites identified in SEM were not detected with the standard scraping and homogenization protocol (Table 12) whereas only two metabolites (2-docosapentaenoylglycerophosphoethanolamine, choline) detected using the standard method were not detected using SEM. The same compound classes were detected using both methods.

TABLE 11

Number of metabolites detected using Standard Method or SEM on cultured cells.

| Method | Number of named compounds |
|---|---|
| Standard | 172 |
| SEM | 236 |

TABLE 12

Metabolites detected by SEM but not by Standard Method.

| | |
|---|---|
| creatinine | 1-heptadecanoylglycerol (1-monoheptadecanoin) |
| creatine phosphate | 1-behenoylglycerol (1-monobehenin) |
| N-formylmethionine | 1-oleoylglycerol (1-monoolein) |
| hypotaurine | 1-myristoylglycerol (1-monomyristin) |
| S-methylglutathione | 2-palmitoylglycerol (2-monopalmitin) |
| 3-phosphoserine | valerate |
| N-acetylthreonine | adenosine 3'-monophosphate (3'-AMP) |
| N6-acetyllysine | N1-methylguanosine |
| p-cresol sulfate | 2'-O-methylguanosine |
| 3-(4-hydroxyphenyl)lactate | N2,N2-dimethylguanosine |
| spermidine | N6-carbamoylthreonyladenosine |
| N-acetylputrescine | allantoin |
| kynurenine | cytosine-2',3'-cyclic monophosphate |
| C-glycosyltryptophan | pseudouridine |
| dimethylarginine (SDMA + ADMA) | alanylphenylalanine |
| urea | glycyltryptophan |
| hydroxyisovaleroyl carnitine | glycylvaline |
| 3-hydroxyisobutyrate | glycylproline |
| erythronate | glycylisoleucine |

TABLE 12-continued

Metabolites detected by SEM but not by Standard Method.

| | |
|---|---|
| Isobar: UDP-acetylglucosamine, UDP-acetylgalactosamine | glycyltyrosine |
| sorbitol | alanylvaline |
| fructose | alanylleucine |
| nicotinamide adenine dinucleotide reduced (NADH) | aspartylphenylalanine |
| nicotinamide riboside | threonylphenylalanine |
| flavin mononucleotide (FMN) | pyroglutamylvaline |
| thiamin (Vitamin B1) | gamma-glutamyltyrosine |
| glycocholate | gamma-glutamylvaline |
| deoxycholate | gamma-glutamylisoleucine |
| deoxycarnitine | gamma-glutamylphenylalanine |
| carnitine | gamma-glutamylthreonine |
| isovalerate | hippurate |
| methyl stearate | EDTA |
| caproate (6:0) | erythritol |

To compare solvent extraction conditions, the following conditions were tested: a SEM incubation time course, PBS washed versus unwashed cells, and formic acid inclusion in the MeOH. Human embryonic kidney cells (HEK293) were grown to confluence in 6-well plates.

For the SEM incubation time course, culture media was discarded, and all cells were quickly washed once with PBS which was subsequently discarded. An 80% room temperature methanol (20% water) solution was added to the cells, and the cells were incubated in the methanol solvent at room temperature for the following incubation times: two, five, or ten minutes. After incubation, the methanol solvent only (leaving cells attached to the plate) was transferred to a clean tube.

To compare PBS washed versus unwashed cells, media was discarded from both plates. One plate was washed quickly with PBS which was subsequently discarded, and the other plate was left unwashed. An 80% room temperature methanol (20% water) solution was added to the cells, and the cells were incubated in the methanol solvent at room temperature for five minutes. The methanol solvent was then transferred to a clean tube.

To compare formic acid addition to the solvent, a 0.1% formic acid solution in 80% MeOH was used. Plates were washed quickly with PBS as described above. An 80% MeOH solution or 80% MeOH, 0.1% formic acid solution was added to the cells and incubated for 5 minutes at room temperature. The solvent extract was transferred to a clean tube.

For all samples, the solvent extracts were evaporated to dryness under a stream of nitrogen gas at 40° C. in a Turbovap LV evaporator (Zymark). The dried extracts were reconstituted in 550 µl methanol:water (80:20) containing internal standards (D,L-2-fluorophenylglycine, D,L-4-chlorophenylalanine, tridecanoic acid, D6 cholesterol). The reconstituted solution was analyzed by metabolomics as described in the general methods section above.

The metabolites recovered from the two methods, SEM and the standard homogenization method, were analyzed by high performance liquid chromatography/tandem mass spectrometry and gas chromatography/mass spectrometry as described above. The number of biochemicals identified as matching to chemical standards in a chemical library are shown in Table 13. Each solvent extraction condition (SEM incubation time course, PBS wash, or 0.1% formic acid addition) yielded essentially the same number, identity, and amount of metabolites, demonstrating that SEM is a robust method for metabolite extraction using a broad range of conditions.

TABLE 13

Number of Metabolites detected using various SEM conditions.

| Method | Total named metabolites |
|---|---|
| MeOH 2 min PBS | 208 |
| MeOH 5 min PBS | 212 |
| MeOH 10 min PBS | 209 |
| MeOH 5 min No PBS | 213 |
| MeOH, 0.1% formic acid 5 min PBS | 197 |

Using SEM for sample processing offered significant advantages over the current method. More metabolites were measured with SEM; metabolites that were not detected using the Standard Method could be measured using SEM. Sample collection was faster and the time required for sample collection was more consistent since the cells did not need to be scraped from the culture vessel and centrifugation was not required. This faster sample processing combined with the immediate quenching of metabolism by the addition of 80% methanol, preserved the metabolic state of the cells and provided a more accurate view of cell physiology and biochemistry at the time of sample collection. Additionally, smaller sample sizes were useful since metabolites were detected at higher levels with SEM, thus, the requirement for fewer cells as starting material allowed the use of smaller cell cultures, further increasing the efficiency and processing capacity with this method. Since SEM is non-destructive, the cells are available for immunocytochemical analysis.

Example 9

PREF: Extraction of Metabolites, Metabolomics Analysis, and Histological Analysis of Various Human Tissue Specimens To evaluate the usefulness of the PREF method for various tissue types, samples of colon, stomach, small bowel, muscle, pancreas, lung, adrenal, and spleen tissues were harvested from beating heart donors and placed directly into 80% room temperature methanol to fix the tissue for histological analysis and to extract metabolites (SEM). Each sample per tissue type was harvested from a different donor. The samples were incubated at room temperature for 24 h-72 h. Following incubation the tissue was removed from the extraction solvent for histological analysis as described in the General Methods section above. The extraction solvent was prepared and analyzed by metabolomics as described in the General Methods section above. Shown in Table 14 are the number of samples tested for each tissue type and the number of metabolites measured in each tissue. Bovine liver tissue samples were included as controls to compare with the Standard Method or SEM. Table 15 lists the metabolites detected in each tissue type.

TABLE 14

Human Tissue Panel.

| Tissue | Number of Samples | Total number of metabolites detected |
|---|---|---|
| Colon | 4 | 340 |
| Stomach | | 334 |
| Small Bowel | | 324 |
| Muscle | | 322 |
| Pancreas | 3 | 311 |

TABLE 14-continued

Human Tissue Panel.

| Tissue | Number of Samples | Total number of metabolites detected |
|---|---|---|
| Lung | 1 | 299 |
| Adrenal | | 283 |
| Spleen | | 262 |
| Bovine Liver (SEM, Control) | 3 | 239 |
| Bovine Liver (Standard Method, Control) | | 230 |

TABLE 15

Metabolites measured in various tissues using SEM.

| METABOLITE | Solvent Extraction Method (SEM) | | | | | | | | | | | Control Bovine LIVER Standard Method |
|---|---|---|---|---|---|---|---|---|---|---|---|---|
| | ADRENAL | COLON | LUNG | MUSCLE | PANCREAS | SMALL BOWEL | SPLEEN | STOMACH | PROSTATE | KIDNEY | Bovine LIVER | |
| glycine | X | X | X | X | X | X | X | X | X | X | X | X |
| sarcosine (N-Methylglycine) | X | X | X | X | X | X | X | X | | | X | X |
| dimethylglycine | | | | X | X | | | X | | X | | |
| serine | X | X | X | X | X | X | X | X | X | | X | X |
| N-acetylserine | | | | | | | | | X | | | |
| homoserine | X | X | X | X | X | X | X | X | | | X | X |
| threonine | X | X | X | X | X | X | X | X | X | X | X | X |
| N-acetylthreonine | X | X | X | X | X | X | X | X | | X | X | |
| betaine | | | | | | | | | X | X | | |
| alanine | X | X | X | X | X | X | X | X | X | X | X | X |
| beta-alanine | X | X | X | X | X | X | X | X | X | X | X | X |
| N-acetylalanine | X | X | X | X | X | X | X | X | | | | |
| aspartate | X | X | X | X | X | X | X | X | X | X | X | X |
| N-carbamoylaspartate | | | | | | | | | | X | | |
| N-acetylaspartate (NAA) | X | X | X | X | X | X | X | X | X | X | | |
| asparagine | X | X | X | X | X | X | X | X | X | | X | X |
| glutamate | X | X | X | X | X | X | X | X | X | X | X | X |
| glutamate, gamma-methyl ester | X | X | X | X | X | X | X | X | X | X | X | X |
| glutamine | X | X | X | X | X | X | X | X | X | X | X | X |
| pyroglutamine | X | X | X | X | X | X | X | X | X | X | X | X |
| gamma-aminobutyrate (GABA) | | | | | | | | | X | X | X | X |
| N-acetyl-aspartyl-glutamate (NAAG) | X | X | X | X | | X | | | X | X | | |
| histidine | X | X | X | X | X | X | X | X | X | X | X | X |
| urocanate | X | X | X | X | | X | | | X | X | X | X |
| histamine | X | X | X | X | X | X | X | X | X | | X | X |
| cadaverine | | X | X | X | X | X | X | X | | | | |
| glutarate (pentanedioate) | X | X | | X | | | | X | X | | | |
| lysine | X | X | X | X | X | X | X | X | X | X | X | X |
| 2-aminoadipate | X | X | X | X | X | X | X | X | X | X | | |
| pipecolate | | X | X | X | X | X | X | X | | X | | |
| saccharopine | | | | X | | | | | | | | |
| N6-acetyllysine | X | X | X | X | X | X | | X | | | X | X |
| glutaroyl carnitine | | X | X | X | | | | X | X | X | X | X |
| phenyllactate (PLA) | X | X | X | X | X | X | | X | | | | |
| phenylalanine | X | X | X | X | X | X | X | X | X | X | X | X |
| p-cresol sulfate | X | X | X | X | X | X | X | X | X | X | X | X |
| O-methyl tyrosine | X | X | X | X | X | X | X | X | | | X | |
| 3,5-diiodo-L-tyrosine | | | | | | | | X | | | | |
| tyrosine | X | X | X | X | X | X | X | X | X | X | X | X |
| 3-(4-hydroxyphenyl)lactate | X | X | X | X | X | X | | X | | | X | |
| noradrenaline | X | | | | | | | | | | | |
| 3-iodotyrosine | | | | | | | | X | X | | | |
| N-acetylphenylalanine | | X | X | X | X | X | | X | | | X | |
| phenylacetylglycine | | X | | | | | | | | | X | X |
| phenylacetylglutamine | X | X | X | X | X | X | X | X | X | X | | |
| phenol sulfate | X | X | X | X | X | X | | X | X | | | |
| kynurenine | X | X | X | X | X | X | | X | X | X | X | X |
| tryptophan | X | X | X | X | X | X | X | X | X | X | X | X |
| tryptophan betaine | | | | | | | | | X | | | |
| serotonin (5HT) | X | X | | | X | X | | X | X | | X | X |
| C-glycosyltryptophan | X | X | X | X | X | X | X | X | X | X | X | X |
| 3-methyl-2-oxobutyrate | | X | | X | | X | | X | | | | |

TABLE 15-continued

Metabolites measured in various tissues using SEM.

| METABOLITE | Solvent Extraction Method (SEM) | | | | | | | | | | | Control Bovine |
|---|---|---|---|---|---|---|---|---|---|---|---|---|
| | AD-RE-NAL | CO-LON | LUNG | MUSCLE | PAN-CREAS | SMALL BOWEL | SPLEEN | STOM-ACH | PROS-TATE | KID-NEY | Bovine LIVER | LIVER Standard Method |
| 3-methyl-2-oxovalerate | | X | X | X | X | X | X | X | | X | | |
| levulinate (4-oxovalerate) | | | | | | | | | X | | | |
| beta-hydroxyisovalerate | | | | | | | | | X | | | |
| isoleucine | X | X | X | X | X | X | X | X | X | X | X | X |
| leucine | X | X | X | X | X | X | X | X | X | X | X | X |
| tigloylglycine | | | | | | | | | | | X | X |
| valine | X | X | X | X | X | X | X | X | X | X | X | X |
| 4-methyl-2-oxopentanoate | X | X | X | X | X | X | | X | | X | | |
| alpha-hydroxyisovalerate | X | X | X | X | X | X | X | X | | | | |
| isobutyrylcarnitine | X | X | X | X | X | X | X | X | X | X | | |
| 2-hydroxy-3-methylvalerate | | X | | | | | | | | | | |
| 2-methylbutyroylcarnitine | X | X | X | X | X | X | | X | X | | | |
| 2-methylbutyrylglycine | | | | | | | | | | | X | X |
| isovalerylcarnitine | X | X | X | X | X | X | X | X | X | | | |
| hydroxyisovaleroyl carnitine | X | X | X | X | X | X | | X | X | | X | |
| tiglyl carnitine | X | X | X | X | X | X | X | X | | | X | X |
| cysteine | X | X | X | | X | X | X | X | X | X | X | X |
| cystine | X | X | X | | X | X | X | X | X | X | X | X |
| methionine sulfoxide | X | X | X | X | X | X | X | X | | | X | X |
| N-formylmethionine | | X | X | X | X | X | | X | | | | |
| hypotaurine | X | X | X | X | X | X | X | X | X | X | X | X |
| taurine | X | X | X | X | X | X | X | X | X | X | X | X |
| S-adenosylmethionine (SAM) | | | | | | | | | | X | | |
| S-adenosylhomocysteine (SAH) | X | X | X | X | X | X | X | X | X | | X | X |
| methionine | X | X | X | X | X | X | X | X | X | X | X | X |
| N-acetylmethionine | X | X | X | X | X | X | X | X | | | X | X |
| 2-hydroxybutyrate (AHB) | X | X | | X | | X | X | X | X | X | X | X |
| dimethylarginine (SDMA + ADMA) | X | X | X | X | X | X | X | X | | | X | X |
| arginine | X | X | X | X | X | X | X | X | X | X | | |
| ornithine | X | X | X | X | X | X | X | X | X | X | X | |
| urea | X | X | X | X | X | X | X | X | X | X | X | X |
| proline | X | X | X | X | X | X | X | X | X | X | X | X |
| 5-aminovalerate | | X | | | | | | | | | | |
| citrulline | | | | | | | | | X | X | | |
| trans-4-hydroxyproline | | | | | | | | | X | X | | |
| 1,3-diaminopropane | | | | | | | | | X | | | |
| creatine | X | X | X | X | X | X | X | X | X | X | X | X |
| creatinine | X | X | X | X | X | X | X | X | X | X | X | X |
| creatine phosphate | | | | X | | | | | | | | |
| 2-aminobutyrate | X | X | X | X | X | X | X | X | X | X | X | X |
| 5-methylthioadenosine (MTA) | X | X | X | X | X | X | X | X | X | X | X | |
| putrescine | X | X | X | X | X | X | X | X | X | | X | X |
| N-acetylputrescine | | | | | | | | | X | | | |
| agmatine | | | | | | | | | X | | | |
| spermidine | X | X | X | X | X | X | X | X | X | | X | X |
| spermine | | | | | | | | | X | | | |
| 4-acetamidobutanoate | | | | | | | | | | X | | |
| glutathione, reduced (GSH) | | X | | X | | | | X | X | X | X | X |
| 5-oxoproline | X | X | X | X | X | X | X | X | X | X | X | X |
| glutathione, oxidized (GSSG) | X | X | X | X | X | X | X | X | X | X | X | |
| cysteine-glutathione disulfide | | | | | | | | | X | X | | |
| ophthalmate | | X | | X | X | X | X | X | X | X | | |
| glycylvaline | X | X | X | X | X | X | X | X | | | X | X |
| glycylproline | | X | X | | X | X | | X | | X | X | X |
| glycylisoleucine | X | X | X | X | X | X | X | X | | | | |
| glycylleucine | X | X | X | X | X | X | X | X | X | X | | X |
| glycylphenylalanine | X | X | X | X | X | X | X | X | | | | |
| glycyltyrosine | X | X | X | X | X | X | X | X | | | | |
| alanylalanine | X | X | X | X | X | X | X | X | | | | X |
| alanylvaline | | X | X | X | X | X | X | X | | | X | X |
| alanylleucine | X | X | X | X | X | X | X | X | X | | X | X |
| alanylglutamate | | | | X | X | X | X | X | | | | |
| alanylisoleucine | X | X | X | X | X | X | X | X | | | | |
| alanylphenylalanine | X | X | X | X | X | X | X | X | | | X | X |
| aspartylphenylalanine | X | X | X | X | X | X | X | X | | | X | X |
| aspartate-glutamate | | X | X | X | X | X | X | X | | | X | X |
| alpha-glutamylglutamate | X | X | X | X | X | X | X | X | | | X | X |
| alpha-glutamylthreonine | X | X | X | X | X | X | X | X | | | | |
| prolylisoleucine | X | X | | | X | X | | X | | | X | |

TABLE 15-continued

Metabolites measured in various tissues using SEM.

| METABOLITE | Solvent Extraction Method (SEM) | | | | | | | | | | Control Bovine |
| --- | --- | --- | --- | --- | --- | --- | --- | --- | --- | --- | --- |
| | AD-RE-NAL | CO-LON | LUNG | MUSCLE | PAN-CREAS | SMALL BOWEL | SPLEEN | STOM-ACH | PROS-TATE | KID-NEY | Bovine LIVER | LIVER Standard Method |
| isoleucylisoleucine | X | X | X | | X | X | X | X | | | | |
| isoleucylleucine | X | X | X | X | X | X | | | | | | X |
| leucylleucine | X | X | X | X | X | X | X | X | | | | |
| pro-hydroxy-pro | X | X | X | X | X | X | | X | | X | X | X |
| phenylalanylphenylalanine | | X | X | | X | X | | X | X | | | |
| pyroglutamylglycine | X | X | | X | X | X | X | X | | | | |
| pyroglutamylglutamine | X | X | | X | X | X | X | X | | | | |
| pyroglutamylvaline | X | X | X | X | X | X | X | X | X | | | |
| valinylglutamate | X | X | X | X | X | X | X | X | | | X | X |
| cyclo(phe-pro) | | X | X | X | X | X | X | X | | | | |
| cyclo(leu-phe) | | X | X | X | X | X | X | X | | | | |
| cyclo(leu-gly) | X | | X | X | X | X | X | X | | | | |
| cyclo(leu-ala) | X | X | X | X | X | X | X | X | | | | |
| cyclo(leu-pro) | X | X | X | X | X | X | X | X | | | | |
| cyclo(gly-phe) | X | | X | | X | X | X | X | | | | |
| carnosine | X | X | | X | X | X | X | X | | | X | X |
| anserine | X | X | X | X | X | X | X | X | | | | |
| gamma-glutamylvaline | X | X | X | X | X | X | X | X | | | X | X |
| gamma-glutamylleucine | X | X | X | X | X | X | X | X | | | X | X |
| gamma-glutamylisoleucine | X | X | X | X | X | X | X | X | | | X | X |
| gamma-glutamylmethionine | X | X | X | X | X | X | X | X | X | | X | X |
| gamma-glutamylglutamate | | X | | | | X | | X | X | X | X | X |
| gamma-glutamylglutamine | X | X | | X | X | X | X | X | X | | X | X |
| gamma-glutamylphenylalanine | X | X | X | X | X | X | X | X | | | X | X |
| gamma-glutamyltyrosine | X | X | X | X | X | X | X | X | | | X | X |
| gamma-glutamyltryptophan | X | X | X | X | X | X | X | X | | | X | X |
| glucosamine | | | | | | | | | | | X | X |
| N-acetylgalactosamine | X | X | X | | X | X | X | X | | | | |
| N-acetylglucosamine | X | X | | | X | X | X | X | X | | | |
| erythronate | X | X | X | X | X | X | X | X | X | X | X | X |
| N-acetylneuraminate | X | X | X | X | X | X | X | X | X | X | X | X |
| fucose | X | X | X | X | X | X | X | X | | | | |
| fructose | X | X | X | X | X | X | X | X | X | X | X | X |
| galactose | X | X | X | X | X | X | X | X | | | X | X |
| maltose | X | X | X | X | X | X | | X | X | | X | X |
| mannitol | X | X | X | X | X | X | X | X | X | X | X | X |
| methyl-alpha-d-mannopyranoside | X | X | X | X | X | X | X | X | | | | |
| mannose | X | X | X | X | X | X | | X | X | | X | X |
| sorbitol | X | X | X | X | X | X | X | X | X | X | X | X |
| sucrose | X | X | X | X | X | X | X | X | X | | | |
| tagatose | | | | | | | | | | | X | |
| trehalose | | | | | | | | | | | X | X |
| maltotriose | | X | X | X | X | | | X | X | | | |
| maltotetraose | | | | | | | | | X | | | |
| raffinose | X | X | X | X | X | X | X | X | | | | |
| 1,5-anhydroglucitol (1,5-AG) | X | X | X | X | X | X | X | X | X | X | | |
| glycerate | X | X | X | X | X | X | X | X | X | X | X | X |
| glucose-6-phosphate (G6P) | | | X | X | | | | | X | X | X | X |
| glucose 1-phosphate | | | | | | | | | X | X | | |
| glucose | X | X | X | X | X | X | X | X | X | X | X | X |
| fructose-6-phosphate | | | X | X | | | | | | | | |
| Isobar: fructose 1,6-diphosphate, glucose 1,6-diphosphate | | | X | | | | | | X | | | |
| 3-phosphoglycerate | | | | X | | | | | X | X | X | |
| pyruvate | X | X | X | X | X | X | X | X | | X | | |
| lactate | X | X | X | X | X | X | X | X | X | X | X | X |
| arabitol | X | X | X | X | X | X | X | X | | X | X | |
| ribitol | X | X | X | X | X | X | X | X | X | X | X | X |
| gluconate | X | X | X | X | X | X | X | X | | X | X | X |
| ribose | X | X | X | X | X | X | X | X | X | | X | X |
| xylitol | X | X | X | X | X | X | X | X | X | X | X | X |
| xylonate | X | X | X | X | X | X | X | X | | | X | X |
| citrate | X | X | X | X | X | X | X | X | X | X | X | |
| cis-aconitate | | | | | | | | | X | | | |
| isocitrate | | | | | | | | | X | | | |
| alpha-ketoglutarate | | | | | | | | | X | | | |
| succinate | X | X | X | X | X | X | X | X | X | X | X | X |
| succinylcarnitine | X | X | X | X | X | X | X | X | X | | | |
| fumarate | X | X | X | X | X | X | X | X | X | X | X | X |

TABLE 15-continued

Metabolites measured in various tissues using SEM.

| METABOLITE | Solvent Extraction Method (SEM) | | | | | | | | | | | Control Bovine |
|---|---|---|---|---|---|---|---|---|---|---|---|---|
| | ADRENAL | COLON | LUNG | MUSCLE | PANCREAS | SMALL BOWEL | SPLEEN | STOMACH | PROSTATE | KIDNEY | Bovine LIVER | LIVER Standard Method |
| malate | X | X | X | X | X | X | X | X | X | X | X | X |
| acetylphosphate | X | X | X | X | X | X | X | X | | | X | X |
| phosphate | X | X | X | X | X | X | X | X | X | X | X | X |
| pyrophosphate (PPi) | X | X | X | X | X | X | X | X | X | X | X | X |
| linoleate (18:2n6) | X | X | X | X | X | X | X | X | X | X | X | X |
| linolenate [alpha or gamma; (18:3n3 or 6)] | X | X | X | X | X | X | | X | X | X | X | X |
| dihomo-linolenate (20:3n3 or n6) | X | X | X | X | X | X | X | X | X | X | X | X |
| eicosapentaenoate (EPA; 20:5n3) | X | X | X | X | X | X | X | X | | | X | X |
| docosapentaenoate (n3 DPA; 22:5n3) | X | X | X | X | X | X | X | X | X | X | X | X |
| docosapentaenoate (n6 DPA; 22:5n6) | X | X | X | X | X | X | X | X | X | X | X | X |
| docosahexaenoate (DHA; 22:6n3) | X | X | X | X | X | X | X | X | X | X | X | X |
| valerate | | X | X | X | | X | | X | | X | | |
| caproate | | | | | | | | | | X | X | |
| heptanoate | | | | | | | | | | X | X | |
| caprylate (8:0) | X | X | X | X | X | X | X | X | X | X | X | |
| pelargonate (9:0) | X | X | X | X | X | X | X | X | X | X | X | X |
| caprate (10:0) | X | X | X | X | X | X | X | X | X | X | X | X |
| laurate (12:0) | X | X | X | X | X | X | X | X | X | X | X | X |
| 5-dodecenoate (12:1n7) | X | X | X | X | X | X | | X | | | X | |
| myristate (14:0) | X | X | X | X | X | X | X | X | | X | X | X |
| myristoleate (14:1n5) | X | X | X | X | X | X | X | X | X | X | X | X |
| pentadecanoate (15:0) | X | X | X | | X | X | | X | | X | X | X |
| palmitate (16:0) | X | X | X | X | X | X | X | X | X | X | X | X |
| palmitoleate (16:1n7) | X | X | X | X | X | X | X | X | X | X | X | X |
| margarate (17:0) | X | X | X | X | X | X | X | X | X | X | X | X |
| 10-heptadecenoate (17:1n7) | X | X | X | X | X | X | X | X | X | X | X | X |
| stearate (18:0) | X | X | X | X | X | X | X | X | X | X | X | X |
| oleate (18:1n9) | X | X | X | X | X | X | X | X | X | X | X | X |
| cis-vaccenate (18:1n7) | X | X | X | X | X | X | | X | X | | X | X |
| conjugated linoleate (18:2n7; 9Z,11E) | | X | | | | | | | | | | |
| stearidonate (18:4n3) | X | X | X | X | X | X | | X | | | X | X |
| nonadecanoate (19:0) | X | X | X | X | X | X | | X | | | X | X |
| 10-nonadecenoate (19:1n9) | X | X | X | X | X | X | X | X | X | | X | |
| arachidate (20:0) | | | | | | | | | | X | | |
| eicosenoate (20:1n9 or 11) | X | X | X | X | X | X | X | X | X | X | X | X |
| dihomo-linoleate (20:2n6) | X | X | X | X | X | X | X | X | X | X | X | X |
| arachidonate (20:4n6) | X | X | X | X | X | X | X | X | X | X | X | X |
| docosadienoate (22:2n6) | | | | | | | | | | X | | |
| adrenate (22:4n6) | X | X | X | X | X | X | X | X | X | X | X | X |
| n-Butyl Oleate | | | | | | | | | | X | | |
| 4-hydroxybutyrate (GHB) | X | X | X | X | X | X | X | X | X | X | | |
| 3-hydroxyoctanoate | X | X | X | X | X | X | X | X | | | | |
| 2-hydroxystearate | | | | | | | | | X | X | | |
| 2-hydroxypalmitate | X | X | X | X | X | X | X | X | X | X | X | X |
| 13-HODE + 9-HODE | X | X | X | X | X | X | X | X | X | | X | X |
| 2-hydroxyglutarate | X | X | X | X | X | X | X | X | X | X | X | X |
| sebacate (decanedioate) | | | | | | | | | | X | | |
| azelate (nonanedioate) | X | X | | X | X | X | | X | | X | | X |
| undecanedioate | | | | | | | | | | X | | |
| hexadecane | | | | | | | | | | X | | |
| 3-carboxy-4-methyl-5-propyl-2-furanpropanoate (CMPF) | | X | | X | | X | | X | | X | X | |
| linoleamide (18:2n6) | | | | | | | | | | X | | |
| 13-methylmyristic acid | | | | | | | | | | X | | |
| methyl palmitate (15 or 2) | X | X | X | X | | X | X | X | X | X | X | X |
| 17-methylstearate | | X | X | X | | | | | | | X | X |
| prostaglandin E2 | | | | | | | | | X | | | |
| 13,14-dihydro-15-keto-prostaglandin a2 | X | X | | | | | | | | | | |
| 8-iso-15-keto-prostaglandin E2 | | | | | | | | | X | | | |
| 12-HETE + 11-HETE + 8-HETE | X | X | X | X | X | X | X | X | | | X | |
| palmitoyl ethanolamide | | | | | | | | | | X | | |
| propionylcarnitine | X | X | X | X | X | X | X | X | X | X | X | X |

TABLE 15-continued

Metabolites measured in various tissues using SEM.

| METABOLITE | Solvent Extraction Method (SEM) | | | | | | | | | | | Control Bovine LIVER Standard Method |
|---|---|---|---|---|---|---|---|---|---|---|---|---|
| | ADRENAL | COLON | LUNG | MUSCLE | PANCREAS | SMALL BOWEL | SPLEEN | STOMACH | PROSTATE | KIDNEY | Bovine LIVER | |
| butyrylcarnitine | X | X | X | X | X | X | X | X | X | X | | |
| valerylcarnitine | X | X | X | X | X | X | X | X | | | | |
| deoxycarnitine | X | X | X | X | X | X | X | X | X | X | X | |
| carnitine | X | X | X | X | X | X | X | X | X | X | X | X |
| 3-dehydrocarnitine | X | X | X | X | X | X | X | X | X | X | X | X |
| acetylcarnitine | X | X | X | X | X | X | X | X | X | X | X | X |
| hexanoylcarnitine | X | X | X | X | X | X | X | X | X | X | | |
| octanoylcarnitine | X | X | X | X | X | X | X | X | | X | | |
| decanoylcarnitine | X | X | X | X | X | X | X | X | | | | |
| laurylcarnitine | | X | X | X | X | X | X | X | | | | X |
| myristoylcarnitine | X | X | X | X | X | X | X | X | | | | |
| palmitoylcarnitine | X | X | X | X | X | X | X | X | | X | X | X |
| stearoylcarnitine | | X | X | X | X | X | X | X | X | X | | X |
| oleoylcarnitine | X | X | X | X | X | | X | X | X | X | X | X |
| cholate | X | X | X | X | X | X | X | X | | | X | X |
| glycocholate | X | X | X | X | X | X | X | X | | | X | X |
| taurocholate | X | X | X | X | X | X | X | X | | | X | X |
| taurochenodeoxycholate | X | X | X | X | X | X | X | X | | | X | X |
| 3-dehydrocholate | | | | | | X | | | | | | |
| deoxycholate | | X | | | | | | X | | | | X |
| taurodeoxycholate | | X | | X | | X | | X | | | X | X |
| glycodeoxycholate | | X | | X | X | X | | X | | | X | X |
| 7-ketodeoxycholate | X | X | X | X | | X | | X | | | | |
| glycochenodeoxycholate | X | X | X | X | X | X | X | X | | | X | X |
| glycolithocholate | | X | | | | X | | | | | X | X |
| taurolithocholate | | X | | X | X | X | | X | | | X | X |
| taurolithocholate 3-sulfate | | | | | | X | | | | | | |
| beta-muricholate | | X | | | | | | | | | | |
| glycocholenate sulfate | X | X | | X | X | X | | X | | | | |
| taurocholenate sulfate | X | X | | | | X | | X | | | | |
| glycoursodeoxycholate | X | X | X | X | X | X | | X | | | | |
| glycoursodeoxycholate | X | X | X | X | X | X | X | X | | | X | X |
| tauroursodeoxycholate | X | X | | X | X | X | X | X | | | X | X |
| 1-octadecanol | | | | | | | | | | X | | |
| choline phosphate | | X | X | X | X | | X | X | X | X | X | X |
| ethanolamine | X | X | X | X | X | X | X | X | X | X | X | X |
| phosphoethanolamine | | X | X | X | X | X | X | X | X | X | | |
| glycerophosphoethanolamine | X | X | X | X | X | X | X | X | X | | X | X |
| glycerol | X | X | X | X | X | X | | X | X | X | X | X |
| choline | | | | | | | | | X | X | | |
| glycerol 3-phosphate (G3P) | X | X | X | X | X | X | X | X | X | X | X | X |
| glycerophosphorylcholine (GPC) | X | X | X | X | X | X | X | X | X | X | X | X |
| cytidine 5'-diphosphocholine | | | | | | | | | X | | | |
| cytidine 5'diphosphoethanolamine | | | | | | | | | X | | | |
| myo-inositol | X | X | X | X | X | X | X | X | X | X | X | X |
| chiro-inositol | | | | | | | | | X | | | |
| inositol 1-phosphate (I1P) | | | | | | | | | X | X | | |
| scyllo-inositol | X | X | X | X | X | X | X | X | X | X | X | X |
| 3-hydroxybutyrate (BHBA) | X | X | X | X | X | X | X | X | X | X | X | X |
| 1,2-propanediol | X | X | X | X | X | X | X | X | X | X | X | X |
| 1-palmitoylglycerophospho-ethanolamine | X | X | X | X | X | X | X | X | X | X | X | X |
| 2-palmitoylglycerophospho-ethanolamine | | | | | | | | | | X | X | |
| 1-heptadecanoylglycerophospho ethanolamine | | | | | | | | | | X | | |
| 1-stearoylglycerophosphoethanolamine | X | X | X | X | X | X | X | X | X | X | X | X |
| 1-oleoylglycerophosphoethanol-amine | | X | X | X | X | X | X | X | X | X | X | X |
| 2-oleoylglycerophosphoethanol-amine | | X | X | X | X | X | | X | X | X | X | X |

TABLE 15-continued

Metabolites measured in various tissues using SEM.

| METABOLITE | Solvent Extraction Method (SEM) | | | | | | | | | | | Control Bovine LIVER Standard Method |
|---|---|---|---|---|---|---|---|---|---|---|---|---|
| | ADRENAL | COLON | LUNG | MUSCLE | PANCREAS | SMALL BOWEL | SPLEEN | STOMACH | PROSTATE | KIDNEY | Bovine LIVER | |
| 1-linoleoylglycerophosphoethanolamine | | X | X | X | X | X | X | X | X | X | X | X |
| 2-linoleoylglycerophosphoethanolamine | | | | | | | | | | X | | |
| 1-arachidonoylglycerophosphoethanolamine | X | X | X | X | X | X | X | X | X | X | X | X |
| 2-arachidonoylglycerophosphoethanolamine | | | | | | | | | | X | X | |
| 2-docosapentaenoylglycerophosphoethanolamine | | | | | | | | | | X | | |
| 2-docosahexaenoylglycerophosphoethanolamine | | | | | | | | | | X | X | |
| 1-stearoylglycerophosphoglycerol | | X | X | X | X | X | | X | X | | X | X |
| 1-myristoylglycerophosphocholine | X | X | X | X | X | X | X | X | | | X | |
| 1-pentadecanoylglycerophosphocholine | | X | X | X | X | X | | X | | | X | X |
| 1-palmitoylglycerophosphocholine | X | X | X | X | X | X | X | X | X | X | X | X |
| 2-palmitoylglycerophosphocholine | X | X | X | X | X | X | X | X | X | X | X | X |
| 1-palmitoleoylglycerophosphocholine | X | X | X | X | X | X | X | X | | | X | X |
| 1-heptadecanoylglycerophosphocholine | | X | | X | X | X | | X | | | X | X |
| 1-stearoylglycerophosphocholine | X | X | X | X | X | X | X | X | X | X | X | X |
| 2-stearoylglycerophosphocholine | | X | X | X | X | X | | X | | | X | X |
| 1-oleoylglycerophosphocholine | X | X | X | X | X | X | X | X | X | X | X | X |
| 2-oleoylglycerophosphocholine | | X | X | X | X | X | X | X | X | X | X | X |
| 1-linoleoylglycerophosphocholine | X | X | X | X | X | X | X | X | X | X | X | X |
| 2-linoleoylglycerophosphocholine | X | X | X | X | X | X | X | X | | X | X | X |
| 1-eicosadienoylglycerophosphocholine | | X | X | X | X | X | X | X | | | | X |
| 1-eicosatrienoylglycerophosphocholine | X | X | X | X | X | X | X | X | | | X | X |
| 1-arachidonoylglycerophosphocholine | X | X | X | X | X | X | X | X | X | X | | |
| 2-arachidonoylglycerophosphocholine | | | | | | | | | | X | X | |
| 1-docosahexaenoylglycerophosphocholine | X | X | X | X | X | X | X | X | | X | X | X |
| 1-palmitoylglycerophosphoinositol | X | X | X | X | X | X | | X | | X | X | X |
| 1-palmitoleoylglycerophosphoinositol | X | X | X | X | X | X | X | X | | | | |

TABLE 15-continued

Metabolites measured in various tissues using SEM.

| METABOLITE | Solvent Extraction Method (SEM) | | | | | | | | | | | Control Bovine LIVER Standard Method |
|---|---|---|---|---|---|---|---|---|---|---|---|---|
| | ADRENAL | COLON | LUNG | MUSCLE | PANCREAS | SMALL BOWEL | SPLEEN | STOMACH | PROSTATE | KIDNEY | Bovine LIVER | |
| 1-stearoylglycerophosphoinositol | X | X | X | X | X | X |   | X | X | X | X | X |
| 1-oleoylglycerophosphoinositol | X | X | X | X | X | X | X | X | X |   | X | X |
| 1-linoleoylglycerophosphoinositol | X | X | X | X | X | X | X | X |   |   | X | X |
| 1-arachidonoyl-glycerophosphoinositol | X | X | X | X | X | X | X | X | X | X | X | X |
| 1-oleoylglycerophosphoserine |   |   |   |   |   |   |   |   | X |   |   |   |
| 1-palmitoylplasmenylethanolamine | X | X | X | X | X | X | X | X | X | X | X | X |
| 1-myristoylglycerol (1-monomyristin) |   |   |   |   |   |   |   |   |   | X |   |   |
| 1-heptadecanoylglycerol (1-monoheptadecanoin) |   |   |   |   |   |   |   |   |   | X |   |   |
| 1-palmitoylglycerol (1-monopalmitin) | X | X | X | X | X | X | X | X |   | X | X | X |
| 2-palmitoylglycerol (2-monopalmitin) |   | X | X | X | X | X |   | X |   | X | X |   |
| 1-stearoylglycerol (1-monostearin) | X | X | X | X | X | X | X | X | X | X | X | X |
| 2-stearoylglycerol (2-monostearin) | X | X | X | X | X | X |   | X |   | X | X |   |
| 1-oleoylglycerol (1-monoolein) | X | X | X | X | X | X | X | X | X | X | X | X |
| 1-behenoylglycerol (1-monobehenin) |   |   |   |   |   |   |   |   |   | X |   |   |
| sphinganine |   |   | X |   |   |   |   |   |   |   |   |   |
| sphingosine | X | X | X | X | X |   | X | X | X | X | X |   |
| palmitoyl sphingomyelin |   | X | X | X |   | X | X | X | X | X | X | X |
| acetylcholine |   |   |   |   |   |   |   |   | X |   |   |   |
| squalene |   |   |   |   |   |   |   |   | X |   |   |   |
| cholesterol |   | X | X | X |   | X | X | X | X | X | X | X |
| 7-beta-hydroxycholesterol |   |   |   |   |   |   |   |   | X |   |   |   |
| dehydroisoandrosterone sulfate (DHEA-S) | X | X |   | X | X | X |   | X |   |   |   |   |
| androsterone sulfate |   | X |   | X | X | X |   | X |   |   |   |   |
| cortisol | X | X |   | X | X |   |   |   |   |   |   |   |
| 21-deoxycortisol |   |   |   |   | X |   |   |   |   |   |   |   |
| 4-androsten-3beta,17beta-diol disulfate 1 | X | X | X | X | X | X |   | X | X |   |   |   |
| 4-androsten-3beta,17beta-diol disulfate 2 | X | X |   | X | X | X |   | X |   |   |   |   |
| pregnen-diol disulfate | X | X | X | X | X | X |   | X |   |   |   |   |
| xanthine | X | X | X | X | X | X | X | X | X | X | X | X |
| xanthosine | X | X | X | X | X | X | X | X | X |   |   | X |
| hypoxanthine | X | X | X | X | X | X | X | X | X | X | X | X |
| inosine | X | X | X | X | X | X | X | X | X | X | X | X |
| 2'-deoxyinosine | X | X | X | X | X | X | X | X |   |   |   |   |
| inosine 5'-monophosphate (IMP) |   |   | X | X |   |   |   |   |   |   |   |   |
| adenine | X | X | X | X | X | X | X | X | X | X | X | X |
| adenosine | X | X | X | X | X | X | X | X | X | X | X | X |
| N1-methyladenosine | X | X | X | X | X | X |   | X |   |   | X |   |
| adenosine 2'-monophosphate (2'-AMP) |   | X |   |   |   |   |   |   |   |   |   |   |
| adenosine 3'-monophosphate (3'-AMP) |   | X |   |   |   |   |   |   |   |   |   |   |
| adenosine 5'-monophosphate (AMP) |   | X | X | X | X | X | X | X | X | X | X | X |
| guanine | X | X | X | X | X | X | X | X | X |   |   | X |
| guanosine | X | X | X | X | X | X | X | X | X | X |   |   |
| guanosine 5' monophosphate (GMP) |   |   |   |   |   |   |   |   |   | X |   |   |
| N2-methylguanosine |   |   |   |   |   |   |   |   | X |   |   |   |
| urate | X | X | X | X | X | X | X | X | X | X | X | X |
| allantoin |   | X |   | X | X | X | X | X | X |   | X | X |
| cytidine | X | X | X | X | X | X | X | X | X |   |   | X |
| cytidine-5'-monophosphate (5'-CMP) |   |   |   |   |   |   |   |   |   | X | X |   |

TABLE 15-continued

Metabolites measured in various tissues using SEM.

| METABOLITE | Solvent Extraction Method (SEM) | | | | | | | | | | | Control Bovine |
|---|---|---|---|---|---|---|---|---|---|---|---|---|
| | AD-RE-NAL | CO-LON | LUNG | MUSCLE | PAN-CREAS | SMALL BOWEL | SPLEEN | STOM-ACH | PROS-TATE | KID-NEY | Bovine LIVER | LIVER Standard Method |
| cytidine-3'-monophosphate (3'-CMP) | X | X | X | X | X | X | X | X | | | X | |
| cytosine-2',3'-cyclic monophosphate | X | X | X | X | X | X | X | X | | | | |
| thymine | | X | | | X | X | X | X | | | | |
| thymidine | X | X | | | X | X | | X | | | | |
| 3-aminoisobutyrate | X | X | X | X | X | X | X | X | | X | X | |
| uracil | X | X | X | X | X | X | X | X | X | X | X | X |
| 5,6-dihydrouracil | X | X | X | X | X | X | X | X | X | X | | X |
| uridine | X | X | X | X | X | X | X | X | X | X | X | X |
| pseudouridine | X | X | X | X | X | X | X | X | X | X | X | X |
| uridine 5'-monophosphate (UMP) | | | | | | | | | X | | | |
| 5-methyluridine (ribothymidine) | X | X | X | X | X | X | X | X | | | | |
| uridine-2',3'-cyclic monophosphate | X | X | X | X | X | X | X | X | | | | |
| methylphosphate | X | X | X | X | X | X | X | X | X | X | X | X |
| gulono-1,4-lactone | | | | | | | | | | | X | X |
| ascorbate (Vitamin C) | | | | | | | | | X | | | X |
| threonate | X | X | X | X | X | X | X | X | X | X | X | |
| arabonate | X | X | X | X | X | X | X | X | X | | X | X |
| heme | | X | | X | | | | | | X | X | |
| coproporphyrin III | | X | | | | | | | | | | |
| nicotinamide | X | X | X | X | X | X | X | X | X | X | X | X |
| nicotinamide adenine dinucleotide (NAD+) | X | X | X | X | X | X | | X | X | X | X | X |
| nicotinamide adenine dinucleotide reduced (NADH) | | X | X | X | | | X | X | X | X | | |
| adenosine 5'-diphosphoribose | | | | | | | | | | X | | |
| 1-methylnicotinamide | | | | | | | | | | X | X | |
| nicotinate | | X | | | | X | X | X | | | X | X |
| pantothenate | X | X | X | X | X | X | X | X | X | X | X | X |
| flavin adenine dinucleotide (FAD) | X | X | X | X | X | X | | | X | X | X | X |
| riboflavin (Vitamin B2) | X | X | X | X | X | X | X | | X | | X | X |
| pyridoxate | X | X | X | X | X | X | | X | | | X | X |
| alpha-tocopherol | | | | | | | | | | X | | |
| gamma-tocopherol | | | | | | | | | | X | | |
| hippurate | | X | | X | X | X | | X | X | X | X | X |
| benzoate | | | | | | | | | | X | X | |
| glycolate (hydroxyacetate) | X | X | X | X | X | X | X | X | X | X | X | X |
| glycerol 2-phosphate | X | X | X | X | X | X | X | X | X | X | X | |
| triethyleneglycol | | | | | | | | | | X | X | |
| heptaethylene glycol | X | X | X | X | X | X | X | X | X | X | | X |
| hexaethylene glycol | X | X | X | X | X | X | X | X | X | X | | |
| octaethylene glycol | | | | | | | | | | X | X | |
| pentaethylene glycol | | | | | | | | | | X | X | |
| tetraethylene glycol | X | X | X | X | | X | | X | X | X | | X |
| trizma acetate | | | | | | | | | | X | | |
| lactobionate | X | X | X | X | X | X | X | X | | | | |
| 3-hydroxypyridine | X | X | X | X | X | X | X | X | | | | X |
| methyl-alpha-glucopyranoside | X | X | X | X | X | X | X | X | X | X | | |
| 2-ethylhexanoate | X | X | X | X | X | X | X | X | | X | X | |
| melamine | | | | | | | | | | X | | |
| 4-acetaminophen sulfate | | | | | | | | | | X | X | |
| 3-(cystein-S-yl)acetaminophen | | | | | | X | | | | | | |
| p-acetamidophenylglucuronide | | | | | | | | | | X | | |
| metoprolol acid metabolite | | | | | | | | | | X | | |
| citalopram | | | | | | | | | | X | | |
| lidocaine | | X | | X | | | | X | | | | |
| gabapentin | | X | | | | | | | | | | |
| sinapate | | | | | | | | | | X | | |
| piperine | X | X | | X | X | X | | X | | | | |
| ergothioneine | X | X | X | X | X | X | X | X | X | X | X | X |
| stachydrine | | | | | | | | | | X | | |
| quebrachitol | | | | | | | | | | X | | |

TABLE 15-continued

Metabolites measured in various tissues using SEM.

| METABOLITE | Solvent Extraction Method (SEM) | | | | | | | | | | | Control Bovine LIVER Standard Method |
|---|---|---|---|---|---|---|---|---|---|---|---|---|
| | ADRENAL | COLON | LUNG | MUSCLE | PANCREAS | SMALL BOWEL | SPLEEN | STOMACH | PROSTATE | KIDNEY | Bovine LIVER | |
| vanillin | X | X | X | X | X | X | | X | X | | | X |
| theobromine | | | | | | | | | X | | | |
| erythritol | X | X | X | X | X | X | X | X | X | X | | |
| 2-phenylpropionate | | X | | | | | | | | | | |

Figure 10:
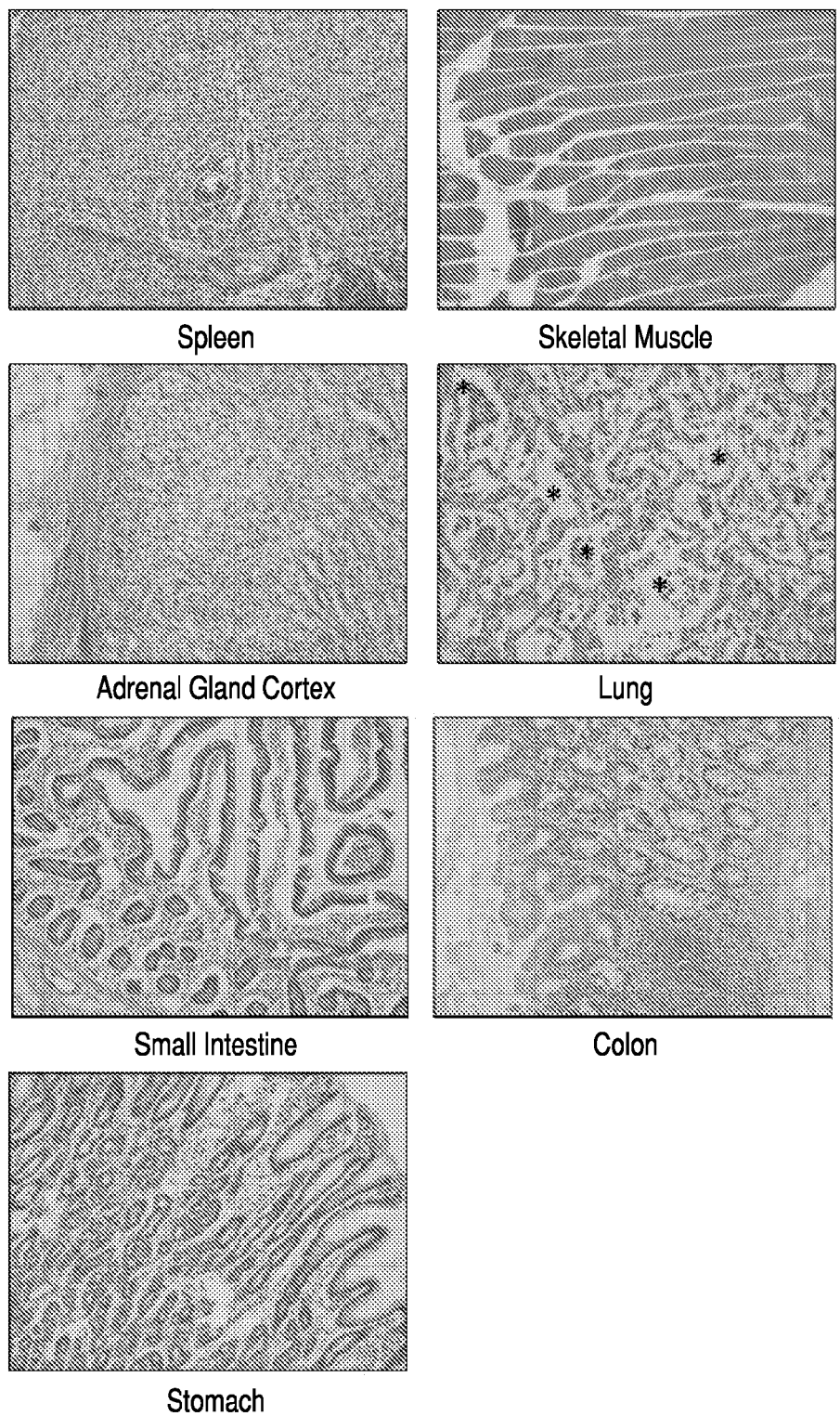
FIG. 10 illustrates histology of spleen, skeletal muscle, adrenal gland cortex, lung, small intestine, colon and lung tissues using the PREF method described in Example 9.

The preservation of cellular architecture based on the histological analysis by a Board Certified pathologist is presented in Table 16. Pictomicrographs from representative sections of each tissue type are presented in FIG. 10. In the image of lung, alveoli are marked with asterisks. These data demonstrate that the PREF method can be successfully used to preserve the tissue architecture for histological evaluation and analyze the metabolites present in an array of tissues with highly diverse cellular morphology and physiology.

TABLE 16

Preservation of cellular architecture using PREF

| Tissue | MeOH (%) | Cellular architecture preserved |
|---|---|---|
| Colon | 80 | Yes |
| Stomach | 80 | Yes |
| Small Bowel | 80 | Yes |
| Muscle | 80 | Yes |
| Pancreas | 80 | Yes |
| Lung | 80 | Yes |
| Adrenal | 80 | Yes |
| Spleen | 80 | Yes |
| Prostate | 80 | Yes |
| Prostate | 70 | Yes |

The invention claimed is:

1. A non-destructive method of extracting and measuring one or more metabolites from a biological sample while preserving the sample for histological analysis, comprising
  (a) immersing the biological sample in a solution consisting of alcohol and water, whereby one or more metabolites present in the biological sample are extracted into the solution;
  (b) physically separating the biological sample from the solution; and
  (c) analyzing the solution by measuring a level(s) of the one or more metabolites extracted into the solution, wherein the extracted metabolites are measured using one or more methods selected from the group consisting of liquid chromatography, gas chromatography, mass spectrometry, and nuclear magnetic resonance; and
  (d) analyzing the biological sample remains analyzable by histological analysis.

2. The method of claim 1, wherein the one or more metabolites are selected from Table 2 and Table 15.

3. The method of claim 1, wherein the biological sample is immersed for a predetermined period of time.

4. The method of claim 1, wherein the one or more metabolites is a xenobiotic.

5. The method of claim 1, wherein the solution consists of water and methanol.

6. The method of claim 5, wherein the solution of methanol and water comprises from 76% to 80% methanol.

7. The method of claim 1, wherein the solution consists of ethanol and water.

8. The method of claim 7, wherein the solution of ethanol and water comprises from 76% to 80% ethanol.

9. The method of claim 1, wherein the biological sample is tumor tissue.

10. The method of claim 1, wherein the biological sample is prostate tissue.

11. The method of claim 1, wherein the biological sample is spinal disc tissue.

12. The method of claim 1, wherein the histological analysis comprises hematoxylin and eosin staining.

13. The method of claim 1, wherein the histological analysis comprises immunohistochemistry.

14. The method of claim 1, wherein the histological analysis comprises cytological analysis.

15. A method for performing histological and metabolite analyses on the same biological sample, comprising:
  (a) immersing the biological sample in a solution consisting of alcohol and water for a pre-determined period of time, whereby one or more metabolites present in the biological sample are extracted into the solution;
  (b) removing the biological sample from the solution;
  (c) measuring a level(s) of the one or more metabolites extracted into the solution, wherein the extracted metabolites are measured using one or more methods selected from the group consisting of liquid chromatography, gas chromatography, mass spectrometry, and nuclear magnetic resonance; and
  (d) performing histological analysis on the biological sample after it has been removed from the solution.

16. The method of claim 15, wherein the one or more metabolites are selected from Table 15.

17. The method of claim 15, wherein the solution consists of methanol and water.

18. The method of claim 17, wherein the solution of methanol and water comprises from 76% to 80% methanol.

19. The method of claim 15, wherein the solution consists of ethanol and water.

20. The method of claim 19, wherein the solution of ethanol and water comprises from 76% to 80% ethanol.

21. The method of claim 15, wherein the biological sample is tumor tissue.

22. The method of claim 15, wherein the biological sample is prostate tissue.

23. The method of claim 15, wherein the histological analysis comprises hematoxylin and eosin staining.

24. A non-destructive method for extracting and measuring metabolites from tissue samples while retaining tissue morphology and utility for subsequent histological analyses, the method comprising (a) extracting metabolites from the tissue sample: (b) measuring the extracted metabolites using one or more methods selected from the group consisting of liquid chromatography, gas chromatography, mass spectrometry, and nuclear magnetic resonance; and (c) analyzing the tissue sample by histological analysis.

* * * * *

UNITED STATES PATENT AND TRADEMARK OFFICE
CERTIFICATE OF CORRECTION

| | | |
|---|---|---|
| PATENT NO. | : 8,980,548 B2 | Page 1 of 1 |
| APPLICATION NO. | : 13/698116 | |
| DATED | : March 17, 2015 | |
| INVENTOR(S) | : Shuster et al. | |

It is certified that error appears in the above-identified patent and that said Letters Patent is hereby corrected as shown below:

In the Claims

Column 49, claim 1, line 58, please delete "remains analyzable"

Signed and Sealed this
Fourteenth Day of July, 2015

Michelle K. Lee
*Director of the United States Patent and Trademark Office*